United States Patent [19]

Ainsworth et al.

[11] Patent Number: 4,478,849

[45] Date of Patent: * Oct. 23, 1984

[54] SECONDARY AMINES, THEIR PREPARATION AND USE IN PHARMACEUTICAL COMPOSITIONS

[75] Inventors: Anthony T. Ainsworth, Cranleigh; David G. Smith, Redhill, both of England

[73] Assignee: Beecham Group Limited, England

[*] Notice: The portion of the term of this patent subsequent to May 11, 1999 has been disclaimed.

[21] Appl. No.: 474,199

[22] Filed: Mar. 10, 1983

Related U.S. Application Data

[60] Division of Ser. No. 382,379, May 27, 1982, , which is a continuation of Ser. No. 51,440, Jun. 25, 1979, abandoned.

[30] Foreign Application Priority Data

Jun. 28, 1978 [GB] United Kingdom ............... 28208/78
Nov. 27, 1978 [GB] United Kingdom ............... 46215/78

[51] Int. Cl.$^3$ ..................... A61K 31/24; A61K 31/195
[52] U.S. Cl. ....................................... 424/285; 560/34; 560/42; 562/430; 562/439; 562/451; 564/50; 564/99; 564/157; 564/165; 424/309; 424/319; 424/320; 424/322; 424/324
[58] Field of Search ............... 424/319, 309, 320, 322, 424/324, 285

[56] References Cited

U.S. PATENT DOCUMENTS 4,086,272  4/1978  Cox et al. ........................... 564/165
4,146,638  3/1979  Renth et al. ......................... 424/319
4,329,358  5/1982  Ainsworth et al. .................. 424/319
4,385,066  5/1983  Ainsworth et al. .................. 424/319

FOREIGN PATENT DOCUMENTS 2135678  3/1972  Fed. Rep. of Germany .
1301134  12/1972  United Kingdom .

Primary Examiner—J. E. Evans
Attorney, Agent, or Firm—Jacobs & Jacobs

[57] ABSTRACT

The compounds of the formula (II):

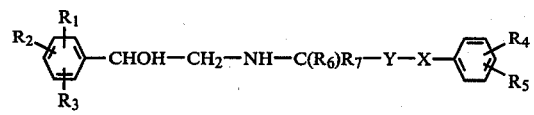

and their pharmaceutically acceptable salts wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; $R_4$ is a carboxylic acid group or a salt, ester or amide thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, or propyl group; X is an oxygen atom or a bond; and Y is an alkylene group of up to 6 carbon atoms or a bond have been found to possess anti-obesity and/or antihyperglycaemic activity.

40 Claims, No Drawings

SECONDARY AMINES, THEIR PREPARATION AND USE IN PHARMACEUTICAL COMPOSITIONS

CROSS-REFERENCE

This is a division of Ser. No. 382,379 filed May 27, 1982 which is a continuation of Ser. No. 051,440, filed June 25, 1979, now abandoned.

The present invention relates to a group of secondary amine derivatives that possess anti-obesity and anti-hyperglycaemic properties, to the method of their preparation and to their use as anti-obesity and/or anti-hyperglycaemic agents which formulated into a pharmaceutical composition.

Certain of the compounds within the formula (I):

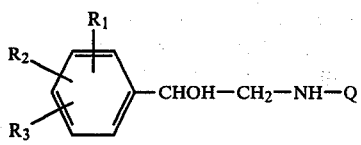

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D. T. Collins et al, J. Med Chem., 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Pat. No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and anti-hyperglycaemic properties. Such compounds may thus be used in the treatment of obesity or hyperglycaemia and can be envisaged as being of particular interest in conditions such as maturity onset diabetes where obesity is often linked with hyperglycaemia.

The present invention provides the compounds of the formula (II):

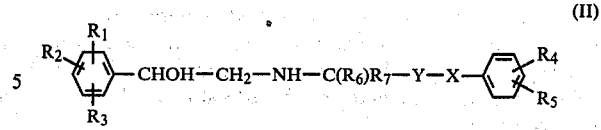

or a pharmaceutically acceptable salt thereof wherein $R_1$ $R_2$ and $R_3$ are as defined in relation to formula (I); $R_4$ is a carboxylic acid group or a salt, ester or amide thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, ethyl or propyl group; $R_7$ is a hydrogen atom or a methyl, ethyl or propyl group; X is an oxygen atom or a bond; and Y is an alkylene group of up to 6 carbon atoms or a bond.

Apt values for $R_1$ include the hydrogen, fluorine and chlorine atoms and the hydroxymethyl, hydroxyl, methoxyl, acetamido, amino, methylsulphonylmethyl, methylsulphonamido, ureido or p-methoxybenzylamino group.

Suitably X in the compounds of the formula (II) is an oxygen atom but more suitably X in the compounds of the formula (II) is a bond.

The moiety Y may be branched if desired, for example in such a manner that it carries one or two methyl groups. However it is more convenient that Y is unbranched. Favoured groups Y are thus of the formula $-(CH_2)_n-$ where n is 0 or an integer from 1 to 6.

A particularly suitable value for $R_2$ is the hydrogen atom.

Aptly $R_3$ is a hydrogen atom. Aptly $R_3$ is a hydroxyl group.

Particularly suitable groups $R_1R_2R_3C_6H_2$ include the 3-ureido-4-hydroxyphenyl; 3-methylsulphonylamino-4-hydroxyphenyl; 3,5-dihydroxyphenyl; 3,4-dihydroxyphenyl; 3-methylsulphony]methyl-4-hydroxyphenyl; 3,5-dichloro-4-aminophenyl; 2-chlorophenyl; 2-methoxy-3,4-dihydroxyphenyl; 3-hydroxymethyl-4-hydroxyphenyl; and 3 (p-methoxybenzyl)amino-4-hydroxyphenyl groups.

A preferred group $R_1R_2R_3C_6H_2$ is the phenyl group.

Another preferred group $R_1R_2R_3C_6H_2$ is the 3,5-dichloro-4-aminophenyl group. A further preferred group $R_1R_2R_3C_6H_2$ is the 3-hydroxymethyl-4-hydroxyphenyl group.

A favourable value for $R_6$ is a hydrogen atom. A further favourable value for $R_6$ is the methyl group. A favourable value for $R_7$ is the hydrogen atom. A further favourable value for $R_7$ is the methyl group. Most favourably $C(R_6)R_7$ is a $CH_2$, $CHCH_3$, or $C(CH_3)_2$ group. The compounds of this invention wherein $C(R_6)R_7$ is a $CH_2$ or $C(CH_3)_2$ group tend to be less potent as anti-obesity agents than those wherein $C(R_6)R_7$ is a $CH(CH_3)$ group but since they possess one less centre as asymmetry they offer the advantage of a slightly easier synthesis. The compounds wherein $C(R_6)R_7$ is a $CH(CH_3)$ group offer the considerable advantage of higher potency as anti-obesity agents.

In the compounds of the invention wherein Y is $-(CH_2)_n-$ group it is mot suitable than n is an integer from 1 to 5 since when n is 0 to 6 the resulting compounds are less potent as anti-obesity agents.

Particularly suitable values for n are 1, 2, 3 and 4 of which 1, 2 and 3 are particularly favourable.

In general when $R_5$ is an electron withdrawing group such as a fluorine atom the resulting compounds are less potent than corresponding compounds wherein $R_5$ is a hydrogen atom or electron releasing group such as a methoxyl group. It follows that a favoured value for $R_5$ is the methoxyl group and a preferred value for $R_5$ is the hydrogen atom.

Apt groups of the formula $R_4$ include those of the sub-formulae (a)–(e):

$$-CO_2H \quad (a)$$

$$-CO_2^-(1_Aq+/q) \quad (b)$$

$$-CO_2R_8 \quad (c)$$

$$-CO.NH_2 \quad (d)$$

$$-CO.NR_9R_{10} \quad (e)$$

wherein $A_{q+}$ is an ion wherein q is aptly 1 or 2; $R_8$ is a group such that $CO_2R_8$ is an ester group; and $R_9$ is a lower alkyl group and $R_{10}$ is a hydrogen atom or a lower alkyl group or is joined to $R_9$ to form a saturated 5, 6 or 7 membered ring.

When used herein the term "lower" means that the group contains not more than 4 carbon atoms.

Particularly, apt values for $R_4$ include those of the sub-formulae (a), (b) or (c).

An especially favoured value for $R_4$ is that of the sub-formula (c). In such compounds it is suitable that the moiety $R_8$ is such that the ester group is hydrolysed in-vivo to yield the corresponding compound wherein $R_4$ is a group of the sub-formula (a).

Particularly suitable values for $R_8$ include lower alkyl groups, lower alkyl groups substituted by a hydroxy group not on the α-carbon atom and groups of the sub-formulae (f) or (g):

$$-CHR_{11}-O-CO-R_{12} \quad (f)$$

(g) [structure showing -CH-O-CO- attached to a phenyl ring bearing $R_{13}$ and $R_{14}$]

wherein $R_{11}$ is a hydrogen atom or a methyl group; $R_{12}$ is a lower alkyl or phenyl group; $R_{13}$ is a hydrogen atom or a methyl or methoxyl group; and $R_{14}$ is a hydrogen atom or a methyl or methoxyl group.

Certain particularly suitable values for $R_8$ include the methyl, ethyl, propyl and butyl groups, for example the methyl group, the ethyl group and the isopropyl group.

The point of attachment of the group $R_4$ is aptly meta- or para- to the point of attachment of the phenyl group to the rest of the molecule.

In order to optimise the anti-obesity effectiveness of the compounds of this invention it is desirable that $R_4$ is in the position para- to the point of attachment of the phenyl group to the rest of the molecule.

One group of preferred compounds of this invention are those of the formula (III):

$$C_6H_5-CHOH-CH_2-NH-C(R_{15})R_{16}-(CH_2)_m-\text{[phenyl]}-CO_2H \quad (III)$$

or a pharmaceutically acceptable salt or ester thereof wherein $R_{15}$ is a hydrogen atom or a methyl group; $R_{16}$ is a hydrogen atom or a methyl group; and m is 1, 2 or 3.

Most suitably $R_{15}$ is a hydrogen atom. Most suitably $R_{16}$ is a methyl group. Favourably m is 1. Favourably m is 2.

Esters of the compound of the formula (III) include those of the sub-formulae (c), (f) and (g) as defined in relation to formula (II).

A further group of preferred compounds of this invention are those of the formula (IV):

$$\text{HO-[phenyl(}HOH_2C\text{)]}-CHOH-CH_2-NH-C(R_{17})R_{18}-(CH_2)_p-\text{[phenyl]}-CO_2H \quad (IV)$$

or a pharmaceutically acceptable salt or ester thereof wherein $R_{17}$ is a hydrogen atom or a methyl group; $R_{18}$ is a hydrogen atom or a methyl group; and p is 1, 2 or 3.

Most suitably $R_{17}$ is a hydrogen atom. Most suitably $R_{18}$ is a methyl group. Favourably p is 1. Favourably p is 2.

Esters of the compounds of the formula (IV) include those of the sub-formulae (c), (f) and (g) as defined in relation to formula (II).

Further particularly suitable compounds of the formula (II) are those of the formula (V):

$$\text{HO-[phenyl(}HOH_2C\text{)]}-CHOH-CH_2NH-CHR_6-CH_2-\text{[phenyl]}-R_4 \quad (V)$$

wherein $R_4$ and $R_6$ are as defined in relation to formula (II).

An especially favoured group of compounds of the formula (II) is that of the formula (VI):

$$\text{HO-[phenyl(}HOH_2C\text{)]}-CHOH-CH_2-NH-CHR_6-CH_2-\text{[phenyl]}-CO_2R_8 \quad (VI)$$

wherein $R_6$ is as defined in relation to formula (II) and $R_8$ is as defined in relation to sub-formula (c).

A further especially favoured group of compounds of the formula (II) is that of the formula (VII):

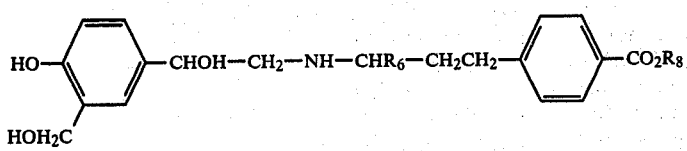

wherein R₆ is as defined in relation to formula (II) and R₈ is defined in relation to sub-formula (c).

Most suitably $R_6$ in relation to formulae (V), (VI) and (VII) is a methyl group.

Certain specific values for $R_8$ include the methyl ethyl, n-propyl, 2-hydroxyethyl, glyceryl, acetoxymethyl, pivaloyloxymethyl, α-ethoxycarbonyloxyethyl and phthalidyl groups. Other specific values for $R_8$ include iso-propyl, n-butyl, iso-butyl, sec-butyl, t-butyl, pentyl, hexyl, benzyl and phenyl.

Apt values of $R_8$ include the methyl, ethyl, n-propyl, 2-hydroxyethyl, glyceryl, acetoxymethyl, pivaloyloxymethyl, α-ethoxycarbonyloxyethyl and phthalidyl groups.

Alkyl groups of 1 to 4 carbon atoms prove convenient moieties for $R_8$.

Certain compounds of this invention particularly worthy of mention in view of their anti-obesity activity include those of Examples 1, 7, 10, 12, 13, 14, 16, 17, 21 (higher melting), 22, 23, 24, 26, 30, 35, 37 and 44. These compounds may be provided as free bases or as pharmaceutically acceptable salts.

Certain compounds of this invention particularly worthy of mention in view of their anti-hyperglycaemic activity include those of Examples 1, 7, 12, 17, 19, 21 (higher melting), 22, 25, 30, 31, 33, 36 and 39. These compounds may be provided as free bases or as pharmaceutically acceptable salts.

Preferred compounds according to this invention include N-[2-(4-carbomethoxyphenyl)-1-methylethyl]-2-hydroxy-2-(4-hydroxy-3-hydroxymethylphenyl)ethanamine and N-[2-(4-carboethoxyphenyl)-1-methylethyl]-2-hydroxy-2-(4-hydroxy-3-hydroxymethylphenyl)ethanamine and their pharmaceutically acceptable acid addition salts.

Other preferred compounds according to this invention include N-[3-(4-carbomethoxyphenyl)-1-methylpropyl]-2-hydroxy-2-(4-hydroxy-3-hydroxymethylphenyl)ethanamine and N-[3-(4-carboethoxyphenyl)-1-methylpropyl]-2-hydroxy-2-(4-hydroxy-3-hydroxymethylphenyl)ethanamine and their pharmaceutically acceptable acid addition salts.

Yet other preferred compounds according to this invention include N-[2-(4-carboxyphenyl)-1-methylethyl]-2-hydroxy-2-(4-hydroxy-3-hydroxymethylphenyl)ethanamine and N-[3-(4-carboxyphenyl)-1-methylpropyl]-2-hydroxy-2-(4-hydroxy-3-hydroxymethylphenyl)ethanamine.

Further preferred compounds according to this invention include N-[2-(4-carboxyphenyl)-1-methylethyl]-2-hydroxy-2-phenylethanamine and N-[3-(4-carboxyphenyl)-1-methylpropyl]-2-hydroxy-2-phenylethanamine.

Yet further preferred compounds according to this invention include N-[2-(4-carbomethoxyphenyl)-1-methylethyl]-2-hydroxy-2-phenylethanamine; N-[3-(4-carbomethoxyphenyl)-1-methylpropyl]-2-hydroxy-2-phenylethanamine; N-[2-(4-carboethoxyphenyl)-1-methylethyl]-2-hydroxy-2-phenylethanamine and N-[3-(4-carboethoxyphenyl)-1-methylpropyl]-2-hydroxy-2-phenylethanamine and their pharmaceutically acceptable acid addition salts.

n-Propyl and iso-propyl esters corresponding to the preceding preferred methyl and ethyl esters are also highly favoured compounds of this invention.

The compounds of this invention wherein $R_4$ is other than a carboxylic acid salt may be provided as acid addition salts. Such salts may be of an organic or inorganic acid but are normally salts with a pharmaceutically acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acid.

The compounds of the formula (II) have a centre of asymmetry at the carbon atom marked with a single asterisk in formula (IIa):

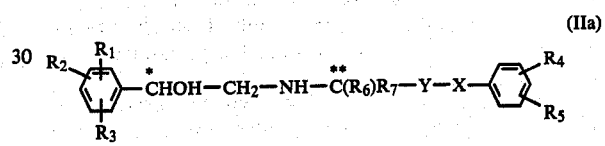

wherein $R_1-R_7$, Y and X are as defined in relation to formula (II). The compounds of the formula (II) have another centre of asymmetry at the carbon atom marked with two asterisks in formula (IIa) when $R_1-R_7$, Y and X are as defined in relation to formula (II) when $R_6$ is different from $R_7$.

The present invention extends to the individual stereoisomeric forms of the compounds of the formula (II) as well as to mixtures thereof. Aptly those compounds of the formula (II) which contain two asymmetric centres are provided in the form of the separated diastereoisomers. Such separated diastereoisomers will of course contain a pair of compounds which are mirror images of each other.

The diastereoisomer of N-[2-(4-carbomethoxyphenyl)-1-methylethyl]-2-hydroxy-2-(4-hydroxy-3-hydroxymethylphenyl)-ethanamine which has the higher melting point has been found to be the more potent diastereoisomer and accordingly is especially preferred. The structurally equivalent diastereoisomers (that is those having the same stereochemistry) of other compounds of the formula (II) wherein $R_6$ is not the same as $R_7$ are similarly apt. Thus, for example, the lower melting diasteriomer of N-[2-(4-carbomethoxyphenyl)-1-methylethyl]-2-hydroxy-2-phenylethanamine (which is the structurally equivalent diastereomer of the afore mentioned) is the more potent diastereoisomer and accordingly is especially preferred.

X-Ray analysis may be used to determine and correlate absolute stereochemistry.

It has been observed that in the $^{13}C$ n.m.r. of compound containing a methyl group on the carbon atom α to the nitrogen atom such as those of Examples 1, 22, 28, 29, 30 and 32, the more active diastereomer is that in which said methyl group appears at higher field (the lower numerical value when expressed in ppm) in d₆DMSO solution. The paired resonances often appear at slightly above 20 ppm (less active) and slightly below 20 ppm (more active, down field from tetramethylsilane. Other paired resonances can occur for the carbon atoms attached directly to the nitrogen atom and the carbon β to nitrogen which carries the hydroxyl group. Again the more active diastereomer of the investigated compounds has the higher field position of the paired resonances.

The present invention also provides a pharmaceutical composition which comprises a compound of this invention and a pharmaceutically acceptable carrier.

The compositions of this invention will normally be formulated for oral administration although compositions formulated for non-oral modes of administration, for example, injection, are also envisaged.

Particularly suitable oral dosage forms are unit dose forms such as tablets or capsules. Other fixed unit dose forms such as powders presented in sachets may also be used.

In accordance with conventional pharmaceutical practice the carrier may comprise a diluent, binder, filler, disintegrant, wetting agent, lubricant, colourant, flavourant or the like.

Typical carriers may therefore comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.01 to 100 mg, more usually 0.2 to 50 mg and favourably 0.5 to 20 mg. Such doses may be taken one to six times a day in a manner such that the total daily dose for a 70 kg adult will generally be about 0.1 to 100 mg and more usually about 2 to 80 mg. The more potent preferred compounds will generally be in unit doses containing 0.1 to 10 mg and more usually 0.25 to 5 mg. Their daily dose will generally be about 0.5 to 20 mg, more usually 1 to 10 mg, for example 2 to 5 mg.

In addition to use in human medicine the compositions of this invention may be used to treat obesity in domestic mammals such as dogs. In general administration to domestic mammals will be by mouth and will usually take place one or two times a day at about 0.025 mg/kg to 2.5 mg/kg, for example 0.1 mg/kg to 2 mg/kg.

The present invention also provides a process for the preparation of a compound of this invention which comprises the reduction of a compound of the formula (VIII):

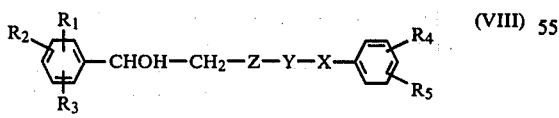

wherein Z is a —N=CR₆ or —NH—C(OH)R₆— group and R₁, R₂, R₃, R₄, R₅, R₆, Y and X are as defined in relation to formula (II) and thereafter if desired forming an addition salt of the initially produced compound of the formula (II).

The reduction of the compound of formula (VIII) may be normally effected by catalytic hydrogenation. Suitable catalysts include noble metal catalysts such as palladium, for example palladium on charcoal or the like such as platinum for example as platinum oxide. A medium or high pressure of hydrogen gas may be used if palladium is the catalyst but it is generally preferred to use an elevated pressure of hydrogen, for example 50-100 p.s.i. If platinum is used as catalyst an atmospheric pressure of hydrogen may be employed. The reaction may be carried out at any convenient non-extreme temperature but it is generally most suitable to use a slightly super ambient temperature such as 30° C. to 100° C., for example 40° C. to 80° C. The hydrogenation may be carried out in a conventional hydrogenation solvent such as a lower alkanol, for example ethanol.

The desired compound may be isolated from the reaction mixture by evaporation of the filtered solution. The initially obtained product may be purified by conventional means, for example by chromatography, crystallisation or the like.

The reduction of the compound of the formula (VIII) may also be effected using a complex hydride such as sodium borohydride.

This reduction is generally carried out in a lower alkanolic solvent, for example methanol if a methyl ester is desired. An approximately ambient temperature may be employed, for example 20° to 30° C.

The desired compound may be obtained from the reaction mixture by evaporation, extraction into a suitable solvent such as ethyl acetate and evaporation. The initially obtained product may be purified as outlined hereinbefore.

The compound of the formula (VIII) may be prepared by the reaction of a compound of the formula (IX):

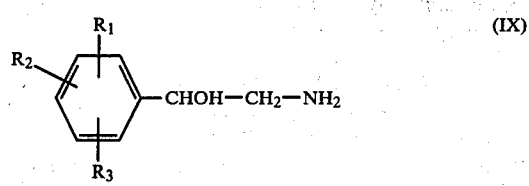

wherein R₁, R₂ and R₃ are as defined in relation to formula (II) with a compound of the formula (X):

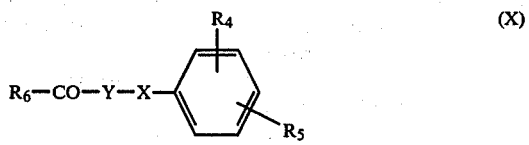

wherein R₄, R₅, R₆, Y and X are as defined in relation to formula (II).

The coupling reaction may be performed in a conventional solvent such as a lower alkanol, for example ethanol. In general the reaction is carried out at an elevated temperature, for example at the reflux temperature.

It is often convenient to prepare and utilize the compound of the formula (VIII) in situ without isolation. In this case the reaction may comprise the hydrogenation of a mixture of a compound of the formula (IX) and a compound of the formula (X) wherein R₁, R₂, R₃, R₄, R₅, R₆, X and Y are as defined in relation to formula (II).

Such a hydrogenation may be carried out under conditions as described for the hydrogenation of a compound of the formula (VIII).

The compounds of the formula (IX) may be prepared in conventional manner, for example as described by D. T. Collins et al, J. Med. Chem., 1970, 13, 674.

The compounds of the formula (II) as hereinbefore defined may also be prepared by the reaction of a compound of the formula (XI):

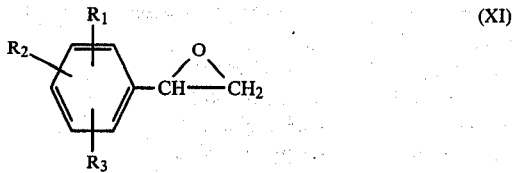

wherein R₁, R₂ and R₃ are as defined in relation to formula (II) with a compound of the formula (XII):

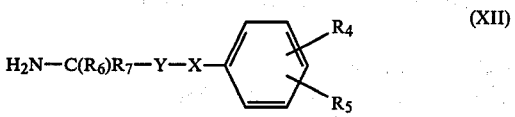

wherein $R_4$, $R_5$, $R_6$, $R_7$, X and Y are as defined in relation to formula (II).

This reaction may be carried out in a solvent such as methylene chloride, chloroform, benzene or the like.

A further method of preparing the compounds of the formula (II) comprises the reduction of a compound of the formula (XIII):

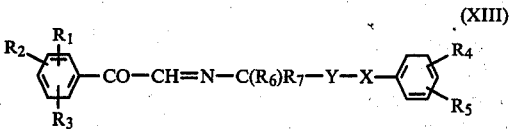

wherein $R_1$, $R_2$, $R_3$, $R_4$, $R_5$, $R_6$, $R_7$, X and Y are as defined in relation to formula (II).

The reduction of the compound of the formula (XIII) may be carried out using a hydride or hydrogen as described for the reduction of the compound of the formula (VIII).

The compound of the formula (XIII) may be prepared by the reaction of a compound of the formula (XIV):

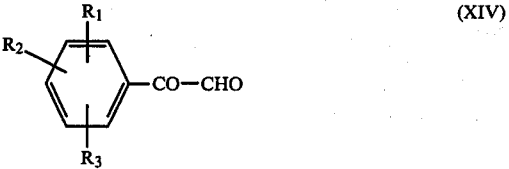

or its hydrate or hemi-acetal of a lower alkanol wherein $R_1$, $R_2$ and $R_3$ are as defined in relation to formula (II), with a compound of the formula (XII)

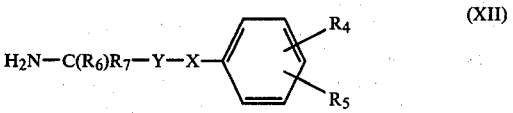

wherein $R_4$, $R_5$, $R_6$, $R_7$, X and Y are as defined in relation to formula (II).

The preceding reaction is generally carried out under conditions that result in the removal of water formed during the reaction. Thus a convenient method is to azeotropically remove the water from a refluxing benzene solution using a Dean and Stark apparatus.

The compound of the formula (XIII) may be obtained from the reaction mixture by evaporation of the solvent and may be purified chromatographically if desired.

Another method of preparing the compounds of the formula (II) comprises the hydrogenation of a compound of the formula (XV):

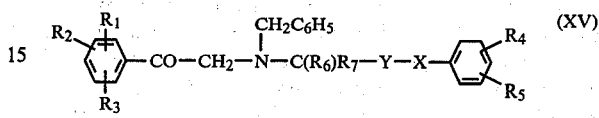

wherein $R_1$, $R_2$, $R_3$, $R_4$, $R_5$, $R_6$, $R_7$, X and Y are as defined in relation to formula (II).

The hydrogenation of the compound of the formula (XV) may take place as described for hydrogenation of the compound of the formula (VIII).

The compound of the formula (XV) may be prepared by the reaction of a compound of the formula (XVI):

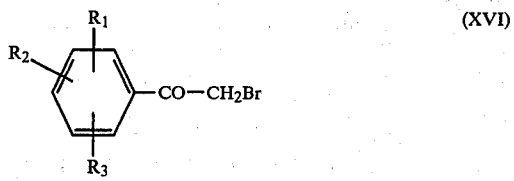

wherein $R_1$, $R_2$ and $R_3$ are as defined in relation to formula with the N-benzyl derivative of a compound of the formula (II).

This reaction may be carried out in a solvent such as acetonitrile or butanone at an elevated temperature, for example under reflux. An acid acceptor is generally present during the reaction for example a tertiary amine which may be a further mole of the N-benzyl derivative of the compound of the formula (XII).

After completion, the reaction mixture may be diluted with ether, filtered and the filtrate evaporated.

Groups $R_1$, $R_2$, $R_3$ and particularly $R_4$, may be modified after the preceding condensation reactions if required; for example a benzyloxy group can be converted to a hydroxy group by hydrogenation, an ester can be hydrolysed to an acid, a benzyl ester can be hydrogenated to yield an acid, a salt of an acid can be esterified by reaction with a reactive chloride, bromide or tosylate, an acid can be esterified by reaction with a hydroxy compound under dehydrating conditions, amides may be prepared from an acid via an acid chloride or similar reaction.

Compounds of the formula (II) containing only one centre of asymmetry may be resolved in known manner, for example using an optically active acid as a resolving agent. Compounds of the formula (II) containing two centres of asymmetry may be separated into their diastereoisomers by fractional crystallisation from a suitable solvent, for example from ethyl acetate. After such separation the individual components of the diastereoisomer may be obtained by resolution in known manner, for example using an optically active acid as a resolving agent.

Suitable optically active acids for use in resolution processes are described in Topics In Stereochemistry, Vol. 6, Wiley Interscience 1971, Allinger N. L. and Eliel W. L. eds.

Stereospecific synthesis may also be employed in order to obtain specific enantiomers. Thus, for example, a single enantiomer of a compound of the formula (IX) may be used to react with a compound of the formula (X) prior to borohydride or catalytic reduction. Similarly a single enantiomer of a compound of the formula (XI) may be used with a compound of the formula (XII). Similarly a single enantiomer of a compound of the formula (XII) (where $R_6$ is not the same as $R_7$) may be used to react with a compound of the formulae (XI) or (XIV) prior to borohydride reduction. The specific enantiomers produced by these processes may then be separated by conventional means such as fractional crystallisation from a suitable solvent, for example, ethyl acetate.

Preparative high pressure liquid chromatography may also be used to separate diastereoisomers, for example, of such compounds as N-[2-(4-carbomethoxyphenyl)-1-methylethyl]-2-hydroxy-2-phenylethanamine, for example using 98:2 dichloromethane:methanol on silica.

The following Examples illustrate the invention. The following Descriptions illustrate the preparation of useful intermediates.

EXAMPLE 1

N-[2-(4-Carbomethoxyphenyl-1-methylethyl]-2-hydroxy-2-(4-hydroxy-hydroxymethylphenyl)ethanamine 1-(4-Carbomethoxyphenyl) propan-2-one (7.0 g) was added to 2-hydroxy-2-(4-hydroxy-3-hydroxymethylphenyl) ethanamine (6.67 g) in ethanol (200 ml) and the solution was refluxed for 4 hours. The solution was cooled to ambient temperature and 10% Pd/C (2 g) was added and the mixture was hydrogenated at 75–85 psi and 50–60° for 12 hours. The solution was filtered, evaporated and the residue taken up in ethyl acetate and filtered again. The filtrate was evaporated, crystallised and recrystallised from benzene to give 7.3 g of the title compound, mp 88°–91° C.

$\tau(d_6DMSO)$ 9.1 (3H, d, J=6 Hz), 6.9–7.8 (5H, m), 6.2 (3H, S), 5.51 (2H, S+1H, t, J=6 Hz), 3.7–5.9 (4H, broad, disappears with D$_2$O), 3.34 (2H, d, J=8 Hz), 2.5–3.18 (3H, m), 2.14 (2H, d, J=8 Hz). $^{13}C$ nmr spectroscopy and glc (by the method of D. W. Selby and G. Munro—Perkin—Elmer Analytical News 13) showed a 1:1 mixture of diastereoisomers.

$^{13}C$ NMR (d$_6$DMSO) ppm 20.01, 1978; 53.96, 53.71; 55.11, 54.84; 71.87, 71.66.

EXAMPLE 2

N-[2-(3-Carbomethoxyphenyl)-1-methylethyl]-2-hydroxy-2-(4-hydroxy-3-hydroxymethylphenyl) ethanamine The title compound (mp 60°–70° ex benzene) was prepared by the process of Example 1 replacing the 1-(4-carbomethoxyphenyl) propan-2-one by 1-(3-carbomethoxyphenyl) propan-2-one. $\tau(d_6DMSO)$ 9.05 (3H, d, J=6 Hz), 6.8–7.8 (5H, m), 6.1 (3H, s), 5.42 (2H, s+1H, t), 4.1–5.7 (4H, broad, disappears with D$_2$O), 2.0–3.3 (7H, m).

EXAMPLE 3

N-[2-(4-Carbomethoxy-3-hydroxyphenyl)-1-methylethyl]-2-hydroxy-2-(4-hydroxy-3-hydroxymethylphenyl)ethanamine The title compound (mp 81°–83° ex benzene) was prepared by the process of Example 1 replacing the 1-(4-carbomethoxyphenyl) propan-2-one by 1-(4-carbomethoxy-3-hydroxyphenyl) propan-2-one. $\tau(d_6DMSO)$ 9.0 (3H, d, J=6 Hz), 6.9–7.6 (5H, m), 6.1 (3H, s), 5.5 (2H, s+1H, t), 3.5–5.2 (5H, broad, disappears with D$_2$O), 2.5–3.35 (5H, m) 2.25 (1H, d, J=8 Hz). $^{13}C$ nmr spectroscopy revealed an approximately 1:1 mixture of diastereoisomers.

EXAMPLE 4

N-[2-(3-Carbomethoxy-4-hydroxyphenyl)-1-methylethyl]-2-hydroxy-2-(4-hydroxy-3-hydroxymethylphenyl) ethanamine The title compound (mp 65°–69° ex benzene) was prepared by the process of Example 1 replacing the 1-(4-carbomethoxyphenyl) propan-2-one by 1-(3-carbomethoxy-4-hydroxyphenyl) propan-2-one $\tau(d_6DMSO)$ 9.05 (3H, d, J=6 Hz), 7.0–7.6 (5H, m), 6.2 (3H, s), 5.5 (2H, s+1H, t), 3.4–5.2 (5H, broad, disappears with D$_2$O), 2.3–3.4 (6H, m).

EXAMPLE 5

N-[2-(3-Carbomethoxy-4-methoxyphenyl)-1-methylethyl]-2-hydroxy-2-(4-hydroxy-3-hydroxymethylphenyl) ethanamine The title compound mp 69°–73° (benzene) was prepared by the process of Example 1 replacing the 1-(4-carbomethoxyphenyl) propan-2-one by 1-(3-carbomethoxy-4-methoxyphenyl) propan-2-one. $\tau(d_6DMSO)$. 9.05 (3H, d, J=6 Hz), 7.0–7.7 (5H, m), 6.2 (3H, s+3H, s), 5.5 (2H, s+1H, t), 4.0–5.8 (4H, broad, disappears with D$_2$O), 2.4–3.4 (6H, m)

EXAMPLE 6

N-[2-(4-Carbomethoxyphenyl)-1-ethylethyl]-2-hydroxy-2-(4-hydroxy-3-hydroxymethylphenyl) ethanamine The title compound, mp 64°–67° (benzene), was prepared as a 1:1 mixture of diastereoisomers by the process of Example 1 replacing 1-(4-carbomethoxyphenyl) propan-2-one by 1-(4-carbomethoxyphenyl)butan-2-one. $\tau(d_6DMSO)$ 9.14 (3H, t, J=6 Hz), 8.9–8.4 (2H, m), 7.6–7.0 (5H, m), 6.18 (3H, s), 5.5 (2H, s+1H, t), 4.3–5.9 (4H, broad, disappears with D$_2$O), 2.05–3.4 (7H, m).

EXAMPLE 7

N-[2-(4-Carbomethoxyphenyl)-1-methylpropyl]-2-hydroxy-2-(4-hydroxy-3-hydroxymethylphenyl) ethanamine The title compound, mp 84.5°–87° (benzene), was prepared as a 2:3 mixture of diastereoisomers by the process of Example 1 replacing 1-(4-carbomethoxyphenyl) propan-2-one by 1-(4-carbomethoxyphenyl)butan-3-one. $\tau(d_6DMSO)$ 8.95 (3H, d), 8.7–8.1 (2H, m), 7.7–7.0 (5H, m), 6.17 (3H, s), 5.49 (2H, s+1H, t), 4.5–5.7 (4H, broad, disappears with D$_2$O), 2.05–3.33 (7H, m).

EXAMPLE 8

N-[2-(4-Carbomethoxyphenoxy)-1-methylethyl]-2-hydroxy-2-(4-hydroxy-3-hydroxymethylphenyl)ethanamine The title compound, mp 60°–68° (benzene) containing ½ mole of benzene of crystallisation, was prepared as a 2:3 mixture of diastereoisomers by the process of Example 1, replacing 1-(4-carbomethoxyphenyl) propan-2-one by 1-(4-carbomethoxyphenoxy) propan-2-one and replacing the 10% Pd/C by PtO$_2$. $\tau$(d$_6$DMSO) 8.95 (3H, d), 7.3 (2H, d), 7.0 (1H, dq), 6.25 (3H, s), 6.15 (2H, d), 5.52 (2H, s+1H, t), 4.0–5.4 (4H, broad, disappears with D$_2$O), 2.18–3.4 (7H, m).

EXAMPLE 9

N-[2-(4-Carbomethoxy-2-fluorophenyl)-1-methylethyl]-2-hydroxy-2-(4-hydroxy-3-hydroxymethylphenyl) ethanamine The title compound, mp 97°–100° (benzene) was prepared as a 1:1 mixture of diastereoisomers by the process of Example 1, replacing 1-(4-carbomethoxyphenyl) propan-2-one by 1-(4-carbomethoxy-2-fluorophenyl) propan-2-one. $\tau$(d$_6$DMSO) 9.1 (3H, d, J=6 Hz), 6.9–7.7 (5H, m), 6.2 (3H, s), 5.45 (2H, s+1H, t), 4.5–5.9 (4H broad, disappears with D$_2$O), 2.2–3.4 (6H, m).

EXAMPLE 10

N-[2-(4-Carbomethoxy-3-methoxyphenyl)-1-methylethyl]-2-hydroxy-2-(4-hydroxy-3-hydroxymethylphenyl)ethanamine The title compound, mp 64°–71° (benzene), was prepared as a 42:58 mixture of diastereoisomers by the process of Example 1, replacing 1-(4-carbomethoxyphenyl) propan-2-one by 1-(4-carbomethoxy-3-methoxyphenyl)propan-2-one. $\tau$(d$_6$DMSO) 9.1 (3H, d, J=6 Hz), 7.0–7.5 (5H, m), 6.3 (3H, s+3H, s), 5.55 (2H, s+1H, t), 4.7–5.8 (4H, broad, disappears with D$_2$O), 2.3–3.45 (6H, m)

EXAMPLE 11

N-[2-(4-N'-Methylcarboxamidophenyl)-1-methylethyl]-2-hydroxy(4-hydroxy-3-hydroxymethylphenyl)ethanamine The title compound was prepared as a foam (acetonitrile) as a 11:9 mixture of diastereoisomers by the process of Example 1, replacing 1-(4-carbomethoxyphenyl) propan-2-one by 1-(4-N-methylcarboxamidophenyl) propan-2-one. $\tau$(d$_6$DMSO) 9.05 (3H, d, J=6 Hz), 7.2 (3H, d, J=4 Hz, collapses to a singlet with D$_2$O), 7.0–7.5 (5H, m), 5.5 (2H, s+1H, t), 4.0–5.5 (4H, broad, disappears with D$_2$O), 3.3 (1H, d, J=8 Hz), 3.0 (1H, d, J=8 Hz), 2.8 (2H, d, J=9 Hz), 2.7 (1H, s), 2.25 (2H, d, J=9 Hz), 1.7 (1H, q, J=4 Hz, disappears with D$_2$O).

EXAMPLE 12

N-[2-(4-Carbomethoxy-2-methoxyphenyl)-1-methylethyl]-2-hydroxy-2-(4-hydroxy-3-hydroxymethylphenyl)ethanamine The title compound, mp 96°–105° (benzene) was prepared as a 3:2 mixture of diastereoisomers by the process of Example 1, replacing 1-(4-carbomethoxyphenyl) propan-2-one by 1-(4-carbomethoxy-2-methoxyphenyl) propan-2-one. $\tau$(d$_6$DMSO) 9.1 (3H, d, J=6 Hz), 7.0–7.5 (5H, m), 6.2 (3H, s+3H, s), 5.55 (2H, s+1H, t) 4.5–5.5 (4H, broad, disappears with D$_2$O), 3.35 (1H, d, J=8 Hz), 3.1–2.4 (5H, m).

EXAMPLE 13

N-[2-(4-Carboisopropoxyphenyl)-1-methylethyl]-2-hydroxy-2-(4-hydroxy-3-hydroxymethylphenyl)ethanamine The title compound, mp 68°–76° (benzene), was prepared as a 1:1 mixture of diastereoisomers by the process of Example 1, replacing 1-(4-carbomethoxyphenyl) propan-2-one by 1-(4-carboisopropoxyphenyl)propan-2-one. $\tau$(d$_6$DMSO) 9.05 (3H, d, J=6 Hz), 8.75 (6H, d, J=6 Hz), 7.0–7.5 (5H, m), 5.55 (2H, s+1H, t), 4.95 (1H, h, J=6 Hz), 4.0–5.5 (4H, broad, disappears with D$_2$O), 3.35 (1H, d, J=8 Hz), 3.05 (1H, d, J=8 Hz), 3.8 (1H, s), 3.75 (2H, d, J=8 Hz), 3.2 (2H, d, J=8 Hz).

EXAMPLE 14

N-[2-(4-Carbomethoxy-3-methylphenyl)-1-methylethyl]-2-hydroxy-2-(4-hydroxy-3-hydroxymethylphenyl)ethanamine The title compound, mp 82°–85° (benzene), was prepared as a 1:1 mixture of diastereoisomers by the process of Example 1, replacing 1-(4-carbomethoxyphenyl) propan-2-one by 1-(4-carbomethoxy-3-methylphenyl) propan-2-one. $\tau$(d$_6$DMSO) 9.05 (3H, d, J=6 Hz), 7.55 (3H, s), 7.2–7.6 (5H, m), 6.25 (3H, s), 5.55 (2H, s+1H, t), 4.55 (4H, broad, disappears with D$_2$O), 3.35 (1H, d, J=8 Hz), 3.05 (1H, d, J=8 Hz), 2.9 (1H, s+1H, s), 2.7 (1H, d, J=8 Hz), 2.25 (1H, d, J=8 Hz).

EXAMPLE 15

N-[2-(4-Pivaloyloxymethyloxycarbonylphenyl)-1-methylethyl]-2-hydroxy-2-(4-hydroxy-3-hydroxymethylphenyl) ethanamine The title compound, mp 55°–57° (benzene), was prepared as a 1:1 mixture of diastereoisomers by the process of Example 1, replacing 1-(4-carbomethoxyphenyl) propan-2-one by 1-(4-pivaloyloxymethyloxycarbonylphenyl) propan-2-one. $\tau$(d$_6$DMSO) 9.1 (3H, d, J=6 Hz), 8.9 (9H, s), 7.0–7.5 (5H, m), 5.55 (2H, s+1H, t), 4.5–5.4 (4H, broad, disappears with D$_2$O), 4.1 (2H, s) 3.35 (1H, d, J=9 Hz), 3.0 (1H, d, J=9 Hz), 2.75 (1H, s), 2.7 (2H, d, J=8 Hz), 2.15 (2H, d, J=8 Hz).

EXAMPLE 16

N-[2-(4-Carboethoxyphenyl)-1-methylethyl]-2-hydroxy-2-(4-hydroxy-3-hydroxymethylphenyl) ethanamine The title compound, mp 92°–96° (benzene), was prepared as a 1:1 mixture of diastereoisomers by the process of Example 1, replacing 1-(4-carbomethoxyphenyl) propan-2-one by 1-(4-carboethoxyphenyl) propan-2-one. $\tau$(d$_6$DMSO) 9.1 (3H, d, J=6 Hz), 8.7 (3H, t, J=7 Hz), 6.85–7.65 (5H, m), 5.75 (2H, q, J=7 Hz), 5.55 (2H, s+1H, t), 4.0–6.0 (4H, broad, disappears with D$_2$O), 3.35 (1H, d, J=8 Hz), 3.0 (1H, d, J=8 Hz), 2.8 (1H, s) 2.75 (2H, d J=9 Hz), 2.2 (2H, d, J=9 Hz).

EXAMPLE 17

N-[2-(4-Carbomethoxyphenyl)-1-methylbutyl]-2-hydroxy-2-(4-hydroxy-3-hydroxymethylphenyl)ethanamine The title compound, mp 73°–75° (benzene), was prepared as a 1:1 mixture of diastereoisomers by the process of Example 1, replacing 1-(4-carbomethoxyphenyl)

propan-2-one by 1-4-carbomethoxyphenyl pentan-4-one. τ(d₆DMSO) 9.05 (3H, d, J=6 Hz), 8.0-8.8 (4H, m), 7.1-7.5 (5H, m), 6.2 (3H, s), 5.5 (2H, s+1H, t), 4.2-5.4 (4H, broad, disappears with D₂O), 3.35 (1H, d, J=8 Hz), 3.0 (1H, d, J=8 Hz), 2.75 (1H, s), 2.7 (2H, d, J=9 Hz), 2.15 (2H, d, J=9 Hz).

EXAMPLE 18

N-[2-(4-Carbomethoxyphenyl)-1-methylmethyl]-2-(4-hydroxy-3-hydroxymethylphenyl)ethanamine A mixture of 4-carbomethoxy-α-methylbenzylamine (0.66 g) and 4-benzyloxy-3-hydroxymethylphenylglyoxal (1.0 g) was refluxed in benzene under Dean and Stark conditions for 2 hours. The solvent was removed under reduced pressure, the residue taken up in methanol and sodium borohydride (1.0 g) added. The solvent was evaporated, ether and water added and the layers separated. The ether layer was dried (MgSO₄) and removal of the solvent gave the title compound (as the O-benzyl derivative) as an oil (1.62 g). This was dissolved in ethanol and hydrogenated at room temperature and atmospheric pressure with 10% Pd/C to give the title compound as a 96:4 mixture of diastereoisomers, mp 102°-105° (benzene). τ(d₆DMSO) 8.82 (3H, d, J=6 Hz), 7.3-7.8 (3H, m), 6.18 (3H, s), 5.52 (2H, s+1H, t), 4.0-7.0 (4H, broad), 3.34 (1H, d, J=8 Hz), 2.97 (1H, dd, J=8 Hz, J=2 Hz), 2.73 (1H, d, J=2 Hz), 2.5 (2H, d, J=8 Hz), 2.07 (2H, d, J=8 Hz).

EXAMPLE 19

N-(2-[4-Carbomethoxyphenyl]-1-methylethyl)-2-(3,4-dihydroxyphenyl)-2-hydroxyethanamine The title compound was obtained as a 8:92 mixture of diastereoisomers, mp 169° (ethyl acetate) by the process of Example 1, replacing 2-hydroxy-2-(4-hydroxy-3-hydroxymethylphenyl)ethanamine by 2-(3,4-dihydroxyphenyl)-2-hydroxyethanamine. τ(d₆DMSO) 8.94 (3H, d, J=6 Hz), 6.90-7.50 (7H, m), 6.03 (3H, s), 5.44 (1H, m), 4.50 (2H, b), 3.10-3.40 (3H, m), 2.54 (2H, d, J=8 Hz), 2.00 (2H, d, J=8 Hz).

EXAMPLE 20

N-[2-(4-Carboxyphenyl)-1-methylethyl]-2-hydroxy-2-(4-hydroxy-3-hydroxymethylphenyl) ethanamine 2-Hydroxy-2-(4-hydroxy-3-hydroxymethylphenyl) ethanamine (1.09 g) and 1-(4-carbobenzyloxyphenyl)propan-2-one (1.6 g) were refluxed in xylene in a Dean and Stark apparatus until the theoretical amount of water had been collected. The solvent was removed, ethanol added and the mixture hydrogenated at 70 psi and 50° for 3 hours using 10% Pd/c as catalyst. Filtration of the catalyst and evaporation of the solvent gave the title compound as a foam τ(d₆DMSO) 8.95 (3H, d, J=7 Hz), 6.8-7.4 (5H, m), 5.5 (2H, s+1H, t), 3.65 (5H, broad), 2.3-3.3 (5H, m), 2.0 (2H, d, J=8 Hz).

EXAMPLE 21

Separation of the diastereoisomers of N-[2-(4-carbomethoxyphenyl)-1-methylethyl]-2-hydroxy-2-(4-hydroxy-3-hydroxymethylphenyl) ethanamine The diastereoisomeric mixture (1:1) prepared as in Example 1 (4 g) was recrystallised from ethyl acetate (200 ml) to give a product (1.53 g) (mp 140.5°-143.5°) enriched in one diastereoisomer. Recrystallisation of this material from ethyl acetate (100 ml) gave 0.8 g of the higher melting diastereoisomer (97% isomeric purity) mp 145.5°-147.5°. Further recrystallisation gave a product of 99.5% isomeric purity, mp 145.5°-147.5°. ¹³C nmr ppm (d₆DMSO) 19.80, 42.78, 51.78, 53.55, 54.81, 58.55, 71.57, 114.11, 124.93, 125.19, 127.28; 127.82, 128.93, 129.17, 129.48, 134.45, 145 54, 153.21, 166.19.

Evaporation of ethyl acetate from the original mother liquor gave an oil which was taken up in benzene and induced to crystallise by scratching to give a solid product (1.81 g) mp 92.5°-94.5°. Recrystallisation of this material from ethyl acetate (100 ml) gave a solid (0.2 g) (mp 137.5°-140.5°) which was discarded. The ethyl acetate was evaporated and ether (20 ml) was added to the residue. This was left at 0° for 3 days and then filtered to give a solid (0.64 g) (mp 97°-100°) which consisted of a 23:77 mixture of diastereoisomers as shown by ¹³C nmr. Recrystallisation of this from ethyl acetate (50 ml) gave a material (0.44 g) which was discarded. Evaporation of the mother liquor gave an oil (0.2 g) which was recrystallised from benzene (10 ml) to give the lower melting diastereoisomer (0.14 g) (mp 70°-73°) having an isomeric purity of 78%. ¹³C nmr ppm (d₆DMSO) 20.10, 42.81, 51.84, 53.83, 55.14, 58.50, 71.82, 114.07, 124.88, 125.17, 127.37, 127.86, 129.00, 129.21, 129.53, 134.54, 145.59, 153.16, 166.19.

EXAMPLE 22

N-(2-[4-Carbomethoxyphenyl]-1-methylethyl)-2-hydroxy-2-phenylethanamine

2-Hydroxy-2-phenylethanamine (2.15 g) and 1-(4-carbomethoxyphenyl)propan-2-one (3.0 g) were heated in refluxing benzene (100 ml) under a Dean and Stark head until the theoretical amount of water had been collected. The solvent was replaced by methanol and the mixture was stirred and cooled during the portionwise addition of sodium borohydride (3.0 g). The mixture was stirred for 2 hours, the solvent was evaporated and the residue was partitioned between water and chloroform. The organic extract was dried, evaporated and recrystallised from hexane, mp 82°-84°, (45:55 mixture of diastereoisomers) and from benzene/hexane, mp 121°-122°, (80:20 mixture of diastereoisomers). τ(CDCl₃) 8.97 (3H, d, J=6 Hz), 6.85-7.60 (7H, m), 6.15 (3H, s), 5.33 (1H, m), 2.81 (2H, d, J=8 Hz), 2.70 (5H, m), 2.04 (2H,d, J=8 Hz). ¹³C NMR (d₆DMSO)ppm. 20.15, 19.90; 53.82, 53.64; 55.03 54.86; 71.91, 71.73.

EXAMPLE 23

N-(2-[4-Carbomethoxy-2-chlorophenyl]-1-methylethyl)-2-hydroxy-2-phenylethanamine The title compound was obtained as the hydrochloride salt as a mixture of diastereoisomers, mp 145°-147° (benzene-hexane) by the process of Example 22, replacing 1-(4-carbomethoxyphenyl)propan-2-one by 1-(4-carbomethoxy-2-chlorophenyl)propan-2-one. τ(CDCl₃) 8.70 (3H, d, J=6 Hz), 6.00-7.10 (5H, m), 6.17 (3H, s), 4.50 (1H, m), 1.60-3.20 (11H, m).

EXAMPLE 24

N-(2-[4-Carbomethoxy-2-methoxyphenyl]-1-methylethyl)-2hydroxy-2-phenylethanamine The title compound was obtained as the hemifumarate as a mixture of diastereoisomers, mp 102°-104° (ethyl acetate) by the process of Example 22, replacing 1-(4-carbomethoxyphenyl) propan-2-one by 1-(4-carbomethoxy-2-methoxypheynyl)propan-2-one.

τ(d₆DMSO) 8.92 (3H, d, J=6 Hz), 6.50–7.60 (7H, m), 6.19 (6H, s), 5.05 (1H, m), 3.45 (2H, s), 2.30–2.80 (6H, m), 1.60–2.00 (4H, m).

EXAMPLE 25

N-(2-[4-Carbomethoxyphenyl]ethyl)-2-hydroxy-2-phenylethanamine

Phenyl glyoxal (0.8 g) and 2-(4-carbomethoxyphenyl) ethanamine (1.1 g) were heated in refluxing benzene (100 ml) under a Dean and stark head until the theoretical amount of water had been collected. The solvent was replaced with methanol and sodium borohydride (2.0 g) was added portionwise with ice cooling. The mixture was stirred for 2 hours, the solvent was evaporated and the residue was partitioned between water and ethyl acetate. The dried organic extract was evaporated and crystallised from benzene/hexane, mp 105°–106°. (CDCl₃) 6.80–7.60 (8H, m), 6.18 (3H, s), 5.34 (1H, m), 2.94 (2H, d, J=8 Hz), 2.77 (5H, m), 2.09 (2H, d, J=8 Hz).

EXAMPLE 26

N-(2-[4-Carbomethoxyphenyl]-1,1-dimethylethyl)-2-hydroxy-2-phenylethanamine

The title compound, mp 125° (benzene) was made by the process of Example 25, replacing 2-(4-carbomethoxyphenyl) ethanamine by 2-(4-carbomethoxyphenyl)-1,1-dimethylethanamine. τ(CDCl₃) 8.98 (6H, s), 6.90–7.60 (6H, m), 6.18 (3H, s), 5.38 (1H, m), 2.87 (2H, d, J=8 Hz), 2.72 (5H, m), 2.12 (2H, d, J=8 Hz).

EXAMPLE 27

N-(2-[4-Carbomethoxyphenyl]ethyl)-2-(2-chlorophyenyl)-2-hydroxyethanamine

The title compound, mp 94°–95° (benzene) was made by the process of Example 25, replacing phenyl glyoxal by 2-chlorophenylglyoxal. τ(CDCl₃) 6.78–7.54 (8H, m), 6.18 (3H, s), 4.89 (1H, m), 2.28–3.03 (6H, m), 2.11 (2H, d, J=8 Hz).

EXAMPLE 28

N-(2-[4-Carbomethoxyphenyl]-1-methylethyl)-2-(2-chlorophenyl)-2-hydroxyethanamine The title compound as a 24:76 mixture of diastereoisomers, mp 109°–110° (hexane) and as pure high mp isomer, mp 115°–117° (benzene) was made by the process of Example 25, replacing phenyl glyoxal by 2-chlorophenyl glyoxal and 2-(4-carboxyphenyl) ethanamine by 2-(4-carbomethoxyphenyl)-1-methylethanamine. τ (CDCl₃) 8.97 (3H, d, J=6 Hz), 6.75–7.72 (7H, m), 6.17 (3H, s), 5.01 (1H, m), 2.34–3.09 (6H, m), 2.11 (2H, d, J=8 Hz). ¹³C NMR (d₆DMSO)ppm. 20.24, 19.84; 68.81, 68.43.

EXAMPLE 29

N-(2-[4-Carbomethoxyphenyl]-1-methylethyl)-2-(4-chlorophenyl)-2-hydroxyethanamine The title compound as a 1:1 mixture of diastereoisomers, mp 134°–135° (benzene), was made by the process of Example 25, replacing phenyl glyoxal by 4-chlorophenyl glyoxal and 2-(4-carbomethoxyphenyl) ethanamine by 2-(4-carbomethoxyphenyl)-1-methylethanamine. τ (CDCl₃/d₆DMSO) 8.97 (3H, d, J=6 Hz), 6.81–7.54 (7H, m), 6.16 (3H, s), 5.40 (1H, m), 2.30–2.92 (6H, m), 2.07 (2H, d, J=8 Hz). ¹³C NMR (d₆DMSO)ppm 20.14, 19.91; 71.28, 71.14.

EXAMPLE 30

N-(2-[4-Carbomethoxyphenyl]-1-methylethyl)-2-(4-amino-3,5-dichlorophenyl)-2-hydroxyethanamine The title compound was obtained as a 10.90 mixture of diastereoisomers, mp 131°–135° (benzene-hexane) and as a 63:37 mixture of diastereoisomers, mp 97°–115° (hexane) by the process of Example 25, replacing phenyl glyoxal by 4-amino-3,5 dichlorophenyl glyoxal and 2-(4-carbomethoxyphenyl) ethanamine by 2-(4-carbomethoxyphenyl)-1-methylethanamine. τ(d₆DMSO-CDCl₃) 8.95 (3H, d, J=6 Hz), 6.90–7.50 (6H, m), 6.10 (3H, s), 5.45 (1H, m), 5.45 (2H, b), 2.90 (2H, s), 2.80 (2H, d, J=8 Hz), 2.10 (2H, d, J=8 Hz). ¹³C NMR (d₆DMSO)ppm 20.17, 19.97.

EXAMPLE 31

N-(2-[4-Carbomethoxyphenyl]-1,1-dimethylethyl)-2-hydroxy-2-(4-hydroxy-3-hydroxymethylphenyl) ethanamine The title compound was obtained as the hydrochloride, mp 103°–106° (ethyl acetate) by the process of Example 33, replacing N-(2-[4-carbomethoxyphenyl]-1-methylethyl)-2-(4-benzyloxy-2-chlorophenyl)-2-hydroxyethanamine by N-(2-[4-carbomethoxyphenyl]-1,1-dimethylethyl)-2-(4-benzyloxy-3-hydroxymethylphenyl)-2-hydroxyethanamine. τ(d₆DMSO) 8.74 (6H, s), 6.60–7.10 (6H, m), 6.14 (3H, s), 5.45 (2H, s), 5.00 (1H, m) 3.16 (2H, d, J=8 Hz), 2.40–3.00 (3H, m), 2.04 (2H, d, J=8 Hz).

EXAMPLE 32

N-(2-[4-Carbomethoxyphenyl]-1-methylethyl)-2-hydroxy-2-(4-methoxyphenyl)ethanamine The title compound was obtained as a mixture of diastereoisomers, mp 87°–89° (ether) by the process of Example 25, replacing phenyl glyoxal by 4-methoxyphenyl glyoxal and 2-(4-carbomethoxphenyl)ethanamine by 2-(4-carbomethoxyphenyl)-1-methylethanamine. τ (CDCl₃) 8.98 (3H, d, J=6 Hz) 6.80–7.70 (7H, m), 6.28 (3H, s), 6.16 (3H, s), 5.42 (1H, m), 3.18 (2H, d, J=8 Hz), 2.60–2.98 (4H, m), 2.08 (2H, d, J=8 Hz). ¹³C NMR (d₆DMSO) ppm. 20.06, 19.84; 71.37, 71.29.

EXAMPLE 33

N-(2-[4-Carbomethoxyphenyl]-1-methylethyl)-2-(2-chloro-4-hydroxyphenyl)-2-hydroxyethanamine N-(2-[4-Carbomethoxyphenyl]-1-methylethyl)-2-(4-benzyloxy-2-chlorophenyl)-2-hydroxyethanamine was hydrogenated in ethanol at atmospheric pressure and room temperature in the presence of 5% palladium on charcoal. The catalyst was removed and the product was recrystallised as the hydrochloride from ethyl acetate as a 28:72 mixture of diastereoisomers, mp 194°–195°. τ (d₆DMSO) 8.79 (3H, d, J=6 Hz), 6.20–7.50 (6H, m), 6.16 (3H, s), 4.67 (1H, m), 2.30–3.30 (5H, m), 2.07 (2H, d, J=8 Hz), 0.67 (1H, br).

EXAMPLE 34

N-(2-[4-Carbomethoxyphenyl]-1-methylethyl)-2-(3-amino-4-hydroxyphenyl-2-hydroxyethanamine The title compound was made as the dihydrochloride, mp 169°–171° (ethanol) as a mixture of diastereoisomers, by the process of example 33, replacing N-(2-[4-carbomethoxyphenyl]-1-methylethyl)-2-(4-benzyloxy-2-chlorophenyl)-2-hydroxyethanamine by N-(2-[4-carbomethoxyphenyl]-1-methylethyl)-2-(4-benzyloxy-3-nitrophenyl)-2-hydroxyethanamine. τ(d₆DMSO) 8.81 (3H, d, J=6 Hz), 6.2-7.3 (7H, m), 5.87 (1H, m), 6.18 (3H, s), 2.2-3.0 (5H, m), 2.08 (2H, d, J=8 Hz), 0.32 (2H, br).

EXAMPLE 35

N-(1-(R)-2-[4-Carbomethoxyphenyl]-1-methylethyl)-2-hydroxy-2-(4-hydroxy-3-hydroxymethylphenyl)ethanamine The title compound was prepared as a 1:1 mixture of diastereoisomers, mp 86.5°-88° (benzene) by the method of Example 33, replacing N-(2-[4-carbomethoxyphenyl]-1-methylethyl-2-(4-benzyloxy-2-chlorophenyl)-2-hydroxyethanamine by N-(1-(R)-2-(4-carbomethoxyphenyl)-1-methylethyl)-2-hydroxy-2-(4-benzyloxy-3-hydroxymethyl)phenylethanamine. τ(DMSO) identical to Example 1.

EXAMPLE 36

N-(1-(S)-2-[4-Carbomethoxyphenyl]-1-methylethyl)-2-hydroxy-2-(4-hydroxy-3-hydroxymethylphenyl)ethanamine The title compound was prepared as a 1:1 mixture of diastereoisomers, mp 88°-89°, (benzene) by the method of Example 35, replacing the 1-(R) isomer by the 1-(S) isomer. τ(DMSO) identical to Example 1.

EXAMPLE 37

N-(2-[4-Carbomethoxyphenyl]-1-methylethyl)-2-(4-hydroxy-3-methanesulphonamidophenyl)-2-hydroxyethanamine The title compound was obtained as a 35:65 mixture of diastereoisomers, mp 133°-140° (ethyl acetate) by the process of Example 33, replacing N-(2-[4-carbomethoxyphenyl]-1-methylethyl)-2-(4-benzyloxy-2-chlorophenyl)-2-hydroxy-ethanamine by N-(2-[4-carbomethoxyphenyl]-1-methylethyl)-2-(4-benzyloxy-3-methanesulphonamidophenyl)-2-hydroxyethanamine. τ(d₆DMSO) 9.10 (3H, d, J=6 Hz), 7.00-7.50 (5H, m), 7.08(3H, s), 6.18(3H, s), 5.50 (1H, m) 4.16 (4H, b), 2.50-3.20 (5H, m) 2.10 (2H, d, J=8 Hz).

EXAMPLE 38

N-(2-[4-Carbomethoxyphenyl]-1-methylethyl)-2-(3-acetamido-4-hydroxyphenyl)-2-hydroxyethanamine The title compound was obtained as the hydrochloride salt as a 33:67 mixture of diastereoisomers, mp 154°-156° (ethyl acetate) by the process of Example 33, replacing N-(2-[4-carbomethoxyphenyl]-1-methylethyl)-2-(4-benzyloxy-2-chlorophenyl)-2-hydroxyethanamine by N-(2-[4-carbomethoxyphenyl]-1-methylethyl)-2-(3-acetamido-4-benzyloxyphenyl)-2-hydroxyethanamine. τ (d₆DMSO) 8.90 (3H, d, J=6 Hz), 7.92 (3H, s), 6.30-7.20 (6H, m), 6.19 (3H, s), 5.10 (1H, m), 3.95 (1H, m), 2.00-3.20 (7H, m), 1.10 (1H, b), 0.55 (1H, s), 0.10 (1H, s).

EXAMPLE 39

N-(2-[4-Carbomethoxyphenyl]-1-methylethyl)-2-(4-hydroxy-3-methylsulphonylmethylphenyl)-2-hydroxyethanamine N-(2-[4-Carbomethoxyphenyl]-1-methylethyl)-2-(4-benzyloxy-3-methylsulphonylmethylphenyl)-2-hydroxyethanamine(2.3 g) was converted to the hydrochloride salt and hydrogenated in ethanol (200 ml) in a Parr hydrogenator at 50 psi and 25° for 2 hours in the presence of 10% palladium on charcoal (0.5 g). The catalyst was removed and the product was isolated as a mixture of diastereoisomers, mp 145°-148° (methanol:ether). τ(d₆DMSO) 8.90 (3H, d, J=6 Hz), 7.2 (3H, s), 6.20-7.10 (6H, m), 6.20 (3H, s), 5.70 (2H, s), 5.00 (1H, m), 390 (1H, b), 2.40-3.10 (5H, m), 2.08 (2H, d, J=8 Hz)., 0.70 (1H, br),-0.10 (1H, br).

EXAMPLE 40

N-(2-[4-Carbomethoxyphenyl]-1-methylethyl)-2-(4-hydroxy-3-ureidophenyl)-2-hydroxyethanamine The title compound was obtained as the hydrochloride salt as a mixture of diastereoisomers by the process of Example 39, replacing N-(2-[4-carbomethoxyphenyl]-1-methylethyl-2-(4-benzyloxy-3-methylsulphonylmethylphenyl)-2-hydroxyethanamine by N-benzyl-N-(2-[4-carbomethoxyphenyl]-1-methylethyl)-2-(4-benzyloxy-3-ureidophenyl)-2-oxoethanamine.
τ(CDCl₃) 9.00 (3H, d, J=6 Hz), 6.70-7.60 (6H, m), 6.30 (3H, s), 5.45 (1H, m), 4.20-5.00 (2H, b), 3.75 (2H, b). 3.25 (2H, s), 2.65 (2H, d, J=8 Hz), 2.00-2.30 (3H, m), 1.75 (1H, b).

EXAMPLE 41

N-(2-[4-Carbomethoxyphenyl]-1-methylethyl)-2-hydroxy-2-(4-hydroxy-3-methylphenyl)ethanamine N-(2-[4-Carbomethoxyphenyl]-1-methylethyl)-2-hydroxy-2-(4-hydroxy-3-hydroxymethylphenyl)ethanamine (3.0 g) was hydrogenated in a mixture of ethanol (200 ml) and chloroform (20 ml) at 1 atmosphere and room temperature in the presence of 5% palladium on charcoal (150 mg) until hydrogen uptake was complete. The catalyst was removed and the product was recrystallised as the hydrochloride from ethyl acetate as a 32.5:67.5 mixture of diastereoisomers, mp 103°-107° (2.0 g). τ(d₆DMSO) 8.88 (3H, d, J=6 Hz), 7.90 (3H, s), 6.10-7.20 (7H, m), 6.20 (3H, s), 5.02 (1H, m), 2.70-3.30 (3H, m), 2.62 (2H, d, J=8 Hz), 2.10 (2H, d, J=8 Hz), 0.62 (1H, br).

EXAMPLE 42

N-(1-(S)-2-[4-Carbomethoxyphenyl]-1-methylethyl)-2-hydroxy-2-(4-hydroxy-3-methylphenyl)ethanamine The title compound was obtained as the hydrochloride as a 1:1 mixture of diastereoisomers, mp 110°-113° (ethyl acetate) by the process of Example 41, replacing N-(2-[4-carbomethoxyphenyl]-1-methylethyl)-2-hydroxy-2-(4-hydroxy-3-hydroxymethylphenyl) ethanamine by the N-(1-(S)-2-[4-carbomethoxyphenyl]-1-methylethyl)isomer. τ (d₆DMSO) identical to Example 41.

EXAMPLE 43

N-(2-[4-Carbomethoxyphenyl]-1,1-dimethylethyl)-2-hydroxy-2-(4-benzyloxy-3-hydroxymethylphenyl)ethanamine The title compound was prepared by the process of Example 25, replacing phenyl glyoxal by 4-benzyloxy-3-hydroxymethylphenyl glyoxal and 2-(4-carbomethoxyphenyl) ethanamine by 2-(4-carbomethoxyphenyl)-1,1-dimethylethanamine. τ (d₆DMSO) 9.06 (6H, s), 7.10-7.60 (5H, m), 6.20 (3H, s), 5.39 (2H, s), 5.00 (1H, m), 4.88 (2H, s), 3.04 (2H, d, J=8 Hz), 2.40-3.00 (10H, m), 2.12 (2H, d, J=8 Hz).

EXAMPLE 44

N-[2-(4-Carboxyphenyl)-1-methylethyl]-2-hydroxy-2-phenylethanamine

2-Hydroxy-2-phenylethanamine (0.68 g) and 1-(4-carbobenzyloxyphenyl)propan-2-one (1.34 g) were refluxed in benzene (50 ml) in a Dean and Stark apparatus for 2 hours. The solvent was removed, tetrahydrofuran (50 ml), benzene (10 ml) and water (3 ml) were added followed by sodium borohydride (0.9 g). The reaction mixture was left at room temperature overnight. The solvent was removed under reduced pressure and the residue partitioned between water and ether. The layers were separated and the organic layer dried (MgSO$_4$). Removal of the solvent gave the title compound as the benzyl ester (1.67 g). This was dissolved in ethanol and hydrogenated at 75 psi and 50° for 4 hours. Filtration and evaporation of the solvent gave the title compound mp 180°–190° (ethyl acetate-methanol). $\tau$ (TFA-d) 8.5 (3H, d, J=7 Hz), 5.85–7.45 (5H, m), 4.72 (1H, broad), 2.6 (7H, m), 1.8 (2H, d, J=8 Hz). $\tau$ (d$_6$DMSO+D$_2$O+NaOD) 9.05 (3H, d, J=7 Hz), 6.9–7.8 (5H, m), 2.85 (2H, d, J=8 Hz), 2.7 (5H, s), 2.17 (2H, d, J=8 Hz).

EXAMPLE 45

N-(2-[4-Carbomethoxyphenyl]-1-methylethyl)-2-(4-benzyloxy-2-chlorophenyl)-2-hydroxyethanamine The title compound as a mixture of diastereoisomers was made by the process of Example 25, replacing phenyl glyoxal by 4-benzyloxy-2-chlorophenyl glyoxal and 2-(4-carbomethoxyphenyl) ethanamine by 2-(4-carbomethoxyphenyl)-1-methylethanamine. $\tau$ (CDCl$_3$) 8.92 (3H, d, J=6 Hz), 6.72–7.71 (7H, m), 6.13 (3H, s), 5.00 (2H, s), 2.33–3.23 (12H, m), 2.03 (2H, d, J=8 Hz).

EXAMPLE 46

N-(2-[4-Carbomethoxyphenyl]-1-methylethyl)-2-(4-benzyloxy-3-nitrophenyl)-2-hydroxyethanamine The title compound was prepared as a mixture of diastereoisomers by the process of Example 25, replacing phenyl glyoxal by 4-benzyloxy-3-nitrophenyl glyoxal and 2-(4-carbomethoxyphenyl)ethanamine by 2-(4-carbomethoxyphenyl)-1-methylethanamine. $\tau$ (CDCl$_3$) 8.93 (3H, d, J=6 Hz), 6.70–7.80 (7H, m), 6.14 (3H, s), 5.40 (1H, m), 4.81 (2H, s), 2.30–3.10 (10H, m), 2.02 (2H, d, J=8 Hz).

EXAMPLE 47

N-(1(R)-2-[4-Carbomethoxyphenyl]-1-methylethyl)-2-hydroxy-2-(4-benzyloxy-3-hydroxymethylphenyl)ethanamine The title compound was prepared as a mixture of diastereoisomers by the method of Example 25, replacing phenyl glyoxal by 4-benzyloxy-3-hydroxymethylphenyl glyoxal and 2-(4-carbomethoxyphenyl) ethanamine by 1-(R)-2-(4-carbomethoxyphenyl)-1-methylethanamine. $\tau$ (CDCl$_3$) 8.98 (3H, d, J=6 Hz), 6.70–7.50 (7H, m), 6.17 (3H, s), 5.43 (1H, m), 5.31 (2H, s), 4.96 (2H, s), 7.16 (2H, d, J=8 Hz), 2.45–3.00 (10H, m), 2.07 (2H, d, J=8 Hz).

EXAMPLE 48

N-(1-(S)-2-[4-Carbomethoxyphenyl]-1-methylethyl)-2-hydroxy-2-(4-benzyloxy-3-hydroxymethylphenyl)ethanamine The title compound was prepared by the method of Example 47 replacing the 1-(R) isomer by the 1-(S) isomer. $\tau$ (CDCl$_3$) identical to Example 47.

EXAMPLE 49

N-(2-[4-Carbomethoxyphenyl]-1-methylethyl)-2-(4-benzyloxy-3-methylsulphonylmethylphenyl)-2-hydroxyethanamine The title compound as a mixture of diastereoisomers was made by the process of Example 25, replacing phenyl glyoxal by 4-benzyloxy-3-methylsulphonylmethylphenyl-glyoxal and 2-(4-carbomethoxyphenyl)ethanamine by 2-(4-carbomethoxyphenyl)-1-methylethanamine. $\tau$ (CDCl$_3$) 8.96 (3H, d, J=6 Hz, 7.40 (3H, s), 6.90–7.60 (5H, m), 6.52 (2H, br), 6.20 (3H, s), 5.69 (2H, s), 5.35 (1H, m), 4.59 (2H, s), 2.40–3.20 (10H, m), 2.07 (2H, d, J=8 Hz).

EXAMPLE 50

N-(2-[4-Carbomethoxyphenyl]-1-(4-benzyloxy-3-methanesulphonamidophenyl)-2-hydroxyethanamine The title compound as a mixture of diastereoisomers was made by the process of Example 25, replacing phenyl glyoxal by 4-benzyloxy-3-methanesulphonamidophenyl glyoxal and 2-(4-carbomethoxyphenyl)ethanamine by 2-(4-carbomethoxyphenyl)-1-methylethanamine. $\tau$ (CDCl$_3$) 8.98 (3H, d, J=6 Hz), 7.20 (3H, s), 6.90–7.50 (5H, m), 6.20 (3H, s), 6.00 (2H, b), 5.4 (1H, m), 4.96 (2H, s), 2.50–3.10 (10H, m), 2.15 (2H, d, J=8 Hz).

EXAMPLE 51

N-(2-[4-Carbomethoxyphenyl]-1-methylethyl)-2-(3-acetamido-4-benzyloxyphenyl)-2-hydroxyethanamine The title compound was obtained as a mixture of diastereoisomers by the process of Example 25, replacing phenyl glyoxal by 3-acetamido-4-benzyloxyphenyl glyoxal and 2(4-carbomethoxyphenyl)ethanamine by 2-(4-carbomethoxyphenyl)-1-methylethanamine. $\tau$ (CDCl$_3$) 8.98 (3H, d, J=6 Hz), 7.94 (3H, s), 7.20 (6H, m), 6.20 (3H, s), 5.40 (1H, m), 4.95 (2H, s), 2.00–2.75 (11H, m), 1.70 (1H, b).

EXAMPLE 52

N-Benzyl-N-(2-[4-carbomethoxyphenyl]-1-methylethyl)-2-(4-benzyloxy-3-ureidophenyl)-2-oxoethanamine 1-(4-Benzyloxy-3-ureidophenyl)-2-bromoethanone (3.1 g) and N-benzyl-(2-[4-carbomethoxyphenyl]-1-methylethanamine) (4.85 g) were heated in refluxing acetonitrile (50 ml) for 2 hours. The solution was diluted with an equal volume of ether, filtered and the filtrate diluted further with ether (200 ml). The solution was washed with water, dried and evaporated to give the title compound, mp 140°–145° (ethyl acetate). $\tau$ (CDCl$_3$) 9.00 (3H, d, J=6 Hz), 6.70–7.60 (3H, m), 6.0–6.4 (4H, m), 6.20 (3H, s), 4.90 (2H, s), 6.32 (2H, b), 2.1–3.3 (17H, m), 1.20 (1H, d, J=2 Hz).

EXAMPLE 53

N-(2-[4-Carbomethoxyphenyl]-1-methylethyl)-2-(3,5-dibenzyloxyphenyl)-2-hydroxyethanamine The title compound was obtained as a mixture of diastereoisomers by the process of Example 25, replacing phenyl glyoxal by 3,5-dibenzyloxyphenylglyoxal and 2-(4-carbomethoxyphenyl)ethanamine by 2-(4-carbomethoxyphenyl)-1-methylethanamine. $\tau$ (CDCl$_3$) 8.95 (3H, d, J=6 Hz), 6.90–7.60 (6H, m), 6.18 (3H, s), 5.02 (4H, s), 3.20–3.60 (3H, m), 2.71 (2H, d, J=8 Hz), 2.40–2.70 (10H, m), 2.02 (2H, d, J=8 Hz).

EXAMPLE 54

N-(2-[4-Carbomethoxyphenyl]-1-methylethyl)-2-(3,5-dihydroxyphenyl)-2-hydroxyethanamine The title compound was obtained as the hydrochloride as a 33:67 mixture of diastereoisomers, mp 118°–120° (ethyl acetate) by the process of Example 41, replacing N-(2-[4-carbomethoxyphenyl]-1-methylethyl)-2-hydroxy-2-(4-hydroxy-3-hydroxymethylphenyl)ethanamine by N-(2-[4-carbomethoxyphenyl]-1-methylethyl)-2-(3,5-dibenzyloxyphenyl)-2-hydroxyethanamine. $\tau$ (d$_6$DMSO) 8.90 (3H, d, J=6 Hz), 6.80–7.70 (7H, m), 6.16 (3H, s), 5.48 (1H, m), 3.60–3.90 (3H, m), 2.62 (2H, d, J=8 Hz), 2.04 (2H, d, J=8 Hz).

EXAMPLE 55

N-[2-(3,4-Dicarbomethoxyphenyl)-1-methylethyl]-2-hydroxy-2-(4-hydroxy-3-hydroxymethylphenyl)ethanamine The title compound (mp 124°–129° ex benzene) was prepared as a 37:63 mixture of diastereoisomers by the process of Example 1, replacing 1-(4-carbomethoxyphenyl)propan-2-one by 1-(3,4-dicarbomethoxyphenyl)propan-2-one. $\tau$ (d$_6$DMSO) 9.1 (3H, d, J=7 Hz), 7.0–7.7 (5H, m), 6.3 (6H, s), 5.5 (2H, s+1H, t), 4.5–5.8 (4H, broad), 2.2–3.5 (6H, m).

EXAMPLE 56

N-[2-(4-carbomethoxyphenyl)-1-methylethyl]-2-hydroxy-2-(4-hydroxy-3-hydroxymethylphenyl)ethanamine A solution of 1-(4-carbomethoxyphenyl)propan-2-one (70 g) and 2-hydroxy-2-(4-hydroxy-3-hydroxymethylphenyl)ethanamine (66.7 g) in ethanol (1750 cm$^3$) was stirred under reflux for 4 hours. The solution was cooled and added to a suspension of 10% palladium on charcoal, (Johnson Matthey type 87L), (20 g) in ethanol (50 cm$^3$) and the resulting mixture hydrogenated at 90 psi and 50°–55° for 18 hours. The mixture was filtered through a Claraid bed, the residue washed with ethanol (about 500 cm$^3$) and the filtrate evaporated under reduced pressure to yield a viscous gum. The gum was dissolved in hot ethyl acetate (100 cm$^3$) and decanted from a small amount of residual brown oil. On standing a white solid crystallised which was filtered off, washed with diethyl ether (about 100 cm$^3$) and dried to give the title compound 56.3 g (43%), mp 139°–141°. ($^{13}$C NMR indicated this to be a 7:3 mixture of diastereoisomers). On standing two further crops of the title compound crystallised from the filtrate giving a total yield of 84.7 g (64.7%).

In a repetition of this experiment the reaction time was extended to 24 hours without significantly changing the yield. In another repetition a mean reaction yield of 72 g (55%) was obtained in three crops as follows: crop 1, 44 g (34%) mp 139°–141°; crop 2, 16 g (12%), mp 118°–120°; crop 3, 12 g (9%), mp 88°–90°. In several experiments the second and/or third crops were obtained by concentrating the filtrate to 600–700 cm$^3$. Occasionally addition of ethyl acetate to the gum resulted in the product crystallising. In some repetitions the initial gum was triturated with diethyl ether prior to recrystallisation from ethyl acetate.

EXAMPLE 57

Higher melting diastereoisomer of N-[2-(4-carbomethoxyphenyl)-1-methylethyl]-2-hydroxy-2-(4-hydroxy-3-hydroxymethylphenyl)ethanamine Several assorted samples of the title compound produced by the process of Example 56 (36 g, mp 133°–144°) were mixed and dissolved in boiling ethyl acetate (1400 cm$^3$), treated with charcoal (1 g) and filtered hot. At 45°–50° the stirred filtrate was seeded with a sample of the pure diastereoisomer, ratio 95:5, (2 g) and stirring continued for 3 hours during which time a white solid crystallised. The solid was collected, washed with diethyl ether (ca. 100 cm$^3$) and dried to yield the title compound 26 g (72% recovery, excluding seed) mp 148°. A glc silylation analysis indicated the product to be a 98:2 mixture of diastereoiomers.

EXAMPLE 58

N-[2-(4-carbomethoxyphenyl)-1-methylethyl]-2-hydroxy-2-phenylethanamine

A mixture of 2-hydroxy-2-phenylethanamine (3.6 g) and 1-(4-carbonethoxyphenyl)propan-2-one (5.0 g) in ethanol (200 ml) was heated under reflux for 1 hour. The solution was hydrogenated in the presence of 10% palladium on charcoal (2.0 g) in a Parr hydrogenator at 60 psi hydrogen pressure and 60° for 6 hours. The catalyst was removed and the solvent was evaporated to give the title compound as a 1:1 mixture of diastereoisomers (7.5 g).

EXAMPLE 59

Separation of diastereoisomers of N-[2-(4-carbomethoxyphenyl)-1-methylethyl]-2-hydroxy-2-phenylethanamine.

The oil of Example 59 was taken up in methanol (7.5 ml) and allowed to stand at 4° for 16 hours. The crystals which were collected, (mp 124°–124.5°) (2.0 g) consisted of a 8:92 mixture of diastereoisomers as shown by $^{13}$C NMR.

A second crop mp 115°–120° (1.5 g) was obtained by addition of ether to the mother liquors. $^{13}$C NMR ppm (d$_6$DMSO): 20.12, 42.85, 51.85, 53.81, 55.03, 71.90, 125.87, 126.67, 127.83, 129.00, 129.54, 144.56, 145.60, 166.21.

The mother liquors were evaporated to an oil which was crystallised from hexane (75 ml) to give colourless crystals (mp 83°–4°) (0.25 g) which consisted of a 86.5:13.5 mixture of diastereoisomers as shown by $^{13}$C NMR. $^{13}$C NMR ppm (d$_6$DMSO): 19.90, 42.87, 51.84, 53.64, 54.86, 71.73, 125.86, 126.69, 127.82, 129.00, 129.53, 144.54, 145.59, 166.20.

EXAMPLE 60

Composition (a) The following ingredients may be mixed together and filled into a two part hard gelatin capsule.
Active ingredient 20 mg Lactose 200 mg This formulation is suitable for administration to humans per os.

(b) The following ingredients may be mixed together and filled into a hard gelatin capsule:

Compound of Example 21 20 mg (higher melting)

Lactose 200 mg

This formulation is suitable for administration to humans per os.

DESCRIPTION 1

1-(4-Carbomethoxyphenyl)propan-2-one

Sodium metabisulphite (131 g) in water (300 ml) was added to 1-(4-carbomethoxyphenyl)propan-2-one oxime (37.5 g) in methanol (200 ml) and the mixture refluxed for 6 hours. The reaction mixture was cooled, concentrated hydrochloric acid (100 ml) added, the mixture extracted with chloroform and the combined chloroform extracts washed with water followed by sodium bicarbonate solution. The chloroform layer was dried (MgSO$_4$) and evaporated to give the title compound as an oil (bp 126°–129°/0.7 mm) which crystallised on standing, (mp 40°–47°). $\tau$ (CDCl$_3$) 7.88 (3H, s), 6.28 (2H, s), 6.14 (3H, s), 2.77 (2H, d, J=8 Hz), 2,04 (2H, d, J=8 Hz).

DESCRIPTION 2

1-(3-Carbomethoxyphenyl)propan-2-one

Concentrated hydrochloric acid (207 ml) was added dropwise over 1 hour to a suspension of 1-(4-carbomethoxyphenyl)-2-nitroprop-1-ene (32.94 g) and iron powder (32.94 g) in methanol at reflux. The solution was refluxed a further 1 hour, cooled, water (500 ml) added and the methanol evaporated. The residue was extracted with ether ($\times$3) and the combined ether layers were washed with water ($\times$3) and sodium bicarbonate solution ($\times$3). The ether layer was dried (MgSO$_4$) and evaporated to give the title compound, 19.1 g (bp 130°–140°/2 mm). $\tau$ (CDCl$_3$) 7.85 (3H, s), 6.28 (2H, s), 6.15 (3H, s), 2.7 (2H, m), 1.9–2.3 (2H, m).

DESCRIPTION 3

1-(4-Carbomethoxy-3-hydroxyphenyl)propan-2-one

The title compound was prepared in an identical manner to that described in Description 2 using 1-(4-carbomethoxy-3-hydroxyphenyl)-2-nitroprop-1-ene. $\tau$ (CDCl$_3$) 7.85 (3H, s), 6.35 (2H, s), 6.09 (3H, s), 3.28 (1H,dd, J=9 Hz, J=2 Hz), 3.20 (1H, d, J=2 Hz), 2.23 (1H, d, J=9 Hz), −0.71 (1H, s, disappears with D$_2$O.)

DESCRIPTION 4

1-(3-Carbomethoxy-4-hydroxyphenyl)propan-2-one

The title compound was prepared in an identical manner to that described in Description 2 using 1-(3-carbomethoxy-4-hydroxyphenyl)-2-nitroprop-1-ene. $\tau$ (CDCl$_3$) 7.85 (3H, s), 6.4 (2H, s), 6.1 (3H, s), 3.1 (1H, d, J=8 Hz), 2.7 (1H, dd, J=8 Hz, J=2 Hz), 2.37 (1H, d, J=2 Hz), −0.75 (1H, s, disappears with D$_2$O).

DESCRIPTION 5

1-(4-Carbomethoxyphenyl)butan-2-one

The title compound was prepared in an identical manner to that described in Description 2 using 1-(4-carbomethoxyphenyl)-2-nitrobut-1-ene. $\tau$ (CDCl$_3$) 9.0 (3H, t, J=7 Hz), 7.53 (2H, q, J=7 Hz), 6.3 (2H, s), 6.15 (3H, s), 3.24 (2H, d, J=8 Hz), 2.05 (2H, d, J=8 Hz).

DESCRIPTION 6

1-(4-Carbomethoxy-3-methylphenyl)propan-2-one

The title compound (bp 130°/0.2 mm) was prepared in an identical manner to that described in Description 2 using 1-(4-carbomethoxy-3-methylphenyl)-2-nitroprop-1-ene. (CDCl$_3$) 7.85 (3H, s), 7.42 (3H, s), 6.3 (2H, s), 6.15 (3H, s), 2.9 (2H, m), 2.05 (1H, d, J=8 Hz).

DESCRIPTION 7

1-(4-Carbomethoxy-2-methoxyphenyl)propan-2-one

The title compound (bp 156°–8°/0.7 mm) was prepared in an identical manner to that described in Description 1 using 1-(4-carbomethoxy-2-methoxyphenyl)-propan-2-one oxime. $\tau$ (CDCl$_3$) 7.85 (3H, s), 6.25 (2H, s), 6.13 (3H, s), 6.07 (3H, s), 2.77 (1H, d, J=8 Hz), 2.37 (1H, s), 2.30 (1H, d, J=8 Hz).

DESCRIPTION 8

1-(4-Carbomethoxy-3-methoxyphenyl)propan-2-one

The title compound (bp 160°/1 mm) was prepared in an identical manner to that described in Description 1 using 1-(4-carbomethoxy-3-methoxyphenyl)propan-2-one oxime. $\tau$ (CDCl$_3$) 7.88 (3H, s), 6.33 (2H, s), 6.17 (3H, s+3H, s), 3.20 (1H, dd, J=8 Hz, J=2 Hz), 3.20 (1H, d, J=2 Hz), 2.25 (1H, d, J=8 Hz).

DESCRIPTION 9

1-(3-Carbomethoxy-4-methoxyphenyl)propan-2-one

A mixture of 1-(3-carbomethoxy-4-hydroxyphenyl)-propan-2-one (3.0 g), iodomethane (5.0 g), potassium carbonate (7.0 g) was refluxed in acetone until tlc showed no starting material (~6 hours). The mixture was cooled, filtered and evaporated. The residue was partitioned between ether and water and the layers separated. The ether layer was dried (MgSO$_4$) and evaporated to give the title compound (3.2 g). $\tau$ (CDCl$_3$) 7.84 (3H, s), 6.35 (2H, s), 6.1 (3H, s), 3.05 (1H, d, J=8 Hz), 2.68 (1H, dd, J=8 Hz, J=2 Hz), 2.36 (1H, d, J=2 Hz).

DESCRIPTION 10

1-(4-Carbomethoxyphenoxy)propan-2-one

A mixture of methyl 4-hydroxybenzoate (30.4 g), chloroacetone (8.5 g) potassium carbonate (54 g) and potassium iodide (33.3 g) was refluxed in acetone for 4 hours. The reaction mixture was cooled, the solids filtered and the solvent evaporated. The residue was partitioned between water and ether, the layers separated and the organic layer dried (MgSO$_4$). Removal of the solvent gave the title compound (36 g). $\tau$ (CDCl$_3$) 7.75 (3H, s), 6.11 (3H, s) 5.39 (2H, s), 3.09 (2H, d, J=9 Hz), 2.0 (2H, d, J=9 Hz).

DESCRIPTION 11

4-Acetonylbenzoic acid

Concentrated hydrochloric acid (367 ml) was added dropwise to a mixture of 1-(4-carboxyphenyl)-2-nitroprop-1-ene (61.17 g) and iron powder (61.17 g) in dioxan (500 ml) at reflux. The heating was continued for 1 hour at the end of addition. The solution was cooled, water added, the dioxan evaporated and the residue extracted with chloroform and dried (MgSO$_4$). Removal of the solvent gave a solid which was recrystallised from ethyl acetate to give 26 g of the title compound. τ (d₆DMSO) 7.83 (3H, s), 6.14 (2H, s), 2.69 (2H, d, J=9 Hz), 2.05 (2H, d, J=9 Hz).

DESCRIPTION 12

4-Acetonylbenzoyl chloride

Thionyl chloride (1.45 ml) was added to 4-acetonylbenzoic acid (3.56 g) in benzene and the mixture refluxed for 1 hour. Benzene was evaporated to give the title compound as a yellow oil, 2.61 g, (bp 135°–140°/0.5 mm). γ (CDCl₃) 7.78 (3H, s), 6.17 (2H, s), 2.63 (2H, d, J=9 Hz), 1.88 (2H, d, J=9 Hz).

DESCRIPTION 13

1-(4-Carboethoxyphenyl)propan-2-one

The title compound was prepared in an identical manner to that described in Description 2 using 1-(4-carboethoxyphenyl)-2-nitroprop-1-ene and replacing the solvent with ethanol. γ (CDCl₃) 8.62 (3H, t, J=7 Hz), 7.87 (3H, s), 6.29 (2H, s), 5.64 (2H, q, J=7 Hz), 2.76 (2H, d, J=9 Hz), 2.0 (2H, d, J=9 Hz).

DESCRIPTION 14

1-(4-Carboisopropoxyphenyl)propan-2-one

Isopropanol (30 ml) was added to 4-acetonylbenzoyl chloride (2.61 g) and the solution left at room temperature 3 days. Removal of the solvent gave the title compound as an oil. γ (CDCl₃) 8.66 (3H, d, J=7 Hz), 7.88 (3H, s), 6.28 (2H, s), 4.78 (1H, h, J=7 Hz), 2.80 (2H, d, J=9 Hz) 2.04 (2H, d, J=9 Hz).

DESCRIPTION 15

1-(4-N-Methylcarboxamidophenyl)propan-2-one

Monomethylamine was passed into a solution of 4-acetonylbenzoyl chloride (4.05 g) in ether. Evaporation of the solvent gave a residue which was partitioned between chloroform and hydrochloric acid (2N) The layers were separated and the organic layer dried. Removal of the solvent gave the title compound (3.51 g). τ (d₆DMSO/CDCl₃) 7.86 (3H, s), 7.15+7.06 (3H, s, s), 6.28 (2H, s),2.80 (2H, d, J=9 Hz), 2.18 (2H, d, J=9 Hz), 2.83 (1H, broad).

DESCRIPTION 16

1-(4-Pivaloyloxymethyloxycarbonylphenyl)propan-2-one

Sodium hydride (0.48 g) was added to 4-acetonylbenzoic acid (3.56 g) in acetonitrile and the solution refluxed for ½ hour. Chloromethyl pivalate (3.02 g) was then added and the mixture refluxed for 22 hours. Acetonitrile was removed, the residue partitioned between ether and water and the organic layer separated and washed with sodium bicarbonate solution (×2). The ether layer was dried (MgSO₄) and evaporated to give the title compound which was crystallised and recrystallised from hexane. τ (CDCl₃) 8.77 (9H, s), 7.82 (3H, s), 6.25 (2H, s), 4.02 (2H, s), 2.73 (2H, d, J=9 Hz), 1.96 (2H, d, J=9 Hz).

DESCRIPTION 17

1-(4-Carbomethoxyphenyl)butan-3-one

Sodium hydride (0.95 g) was added to ethyl acetoacetate (5.2 g) in tetrahydrofuran and the solution was heated for ½ hour. Methyl 4-bromomethylbenzoate (9.36 g) in tetrahydrofuran was added and the solution refluxed for 20 hours. The solvent was removed and the residue partitioned between ether and water. The organic layer was dried (MgSO₄) and evaporated to give the intermediate β-keto ester (9.4 g) as a mixture of keto-enol tautomers. To this was added 5% sodium hydroxide solution (120 ml) and the mixture stirred at room temperature for 4 hours. The aqueous layer was extracted with ether, made acidic and refluxed for 1 hour. The solution was cooled to room temperature during which time crystals of 1-(4-carboxyphenyl)butan-3-one were deposited. Reflux of this with methanol containing sulphuric acid for 15 hours gave the title compound 3.26 g, bp 126°–132°/0.4 mm. τ (CDCl₃) 7.9 (3H, s), 6.85–7.45 (4H, m), 6.15 (3H, s), 2.85 (2H, d, J=9 Hz), 2.1 (2H, d, J=9 Hz).

DESCRIPTION 18

1-(4-Carbomethoxyphenyl)pentan-4-one

The title compound (bp 148°–151°/0.8 mm) was prepared in an identical manner to that described in Description 17 using methyl 4-(2-bromoethyl)benzoate (prepared in an analagous manner to the ethyl ester—E. L. Foreman and S. M. McElvain, J. Amer. Chem. Soc. 1940, 62, 1435. γ (CDCl₃) 8.0–8.2 (2H, m), 7.86 (3H, s), 7.1–7.7 (4H, m), 6.1 (3H, s), 2.7 (2H, d, J=9 Hz), 1.95 (2H, d, J=9 Hz).

DESCRIPTION 19

1-(4-Carbomethoxy-2-fluorophenyl)propan-2-one

The title compound, bp 122°–128°/1 mm, was prepared in an identical manner to that described in Description 2 using 1-(4-carbomethoxy-2-fluorophenyl)-2-nitroprop-1-ene. τ (CDCl₃) 7.78 (3H, s), 6.2 (2H, s), 6.1 (3H, s), 2.72 (1H, dd, J=8 Hz,J=2 Hz), 2.1–2.4 (2H, m).

DESCRIPTION 20

1-(4-Carbomethoxy-2-chlorophenyl)propan-2-one

The title compound was prepared in an identical manner to that described in Description 1 using 1-(4-carbomethoxyphenyl)propan-2-one oxime. τ (CDCl₃) 7.82 (3H, s), 6.15 (3H, s+2H, s), 1.85–2.85 (3H, m).

DESCRIPTION 21

1-(4-Carbomethoxyphenyl)octan-7-one n-Butyl-lithium (1 equivalent) was added dropwise under nitrogen to a solution of heptan-1-yne-7-one ethylene ketal (5.0 g) in ether at ice salt temperature and gave an intense red colour. The solution was stirred at this temperature for 40 minutes. This solution was added to a solution of 4-carbomethoxybenzaldehyde (5.3 g) at the same temperature and produced a grey precipitate. The mixture was left to warm to room temperature. Water was added, the layers separated and the ether layer dried (MgSO₄). Removal of the solvent gave an oil which was chromatographed on silica (300 g). Elution with ether gave 1-(4-carbomethoxyphenyl)-1-hydroxyoctan-2-yne-7-one ethylene ketal as a clear oil (5 g). τ (CDCl₃) 8.77 (3H, s), 8.35 (4H, m), 7.75 (2H, t, J=7 Hz), 6.85 (1H, broad), 6.16 (3H, s+4H, s), 4.52 (1H, s), 2.45 (2H, d, J=8 Hz), 2.0 (2H, d, J=8 Hz).

The above oil was dissolved in ethanol and hydrogenated at room temperature and atmospheric pressure using 10%Pd/C until the theoretical amount of hydrogen was absorbed. The mixture was filtered, evaporated and the residue treated with methanol/5N HCl at room temperature for 1 hour to give the title compound. γ (CDCl₃) 8.05–9.05 (8H, m), 7.92 (3H, s), 7.61 (2H, t, J=7 Hz), 7.36 (2H, t, J=7 Hz), 6.16 (3H, s), 2.8 (2H, d, J=8 Hz) 2.05 (2H, d, J=8 Hz).

DESCRIPTION 22

1-(4-Carbobenzyloxyphenyl)propan-2-one

4-Acetonylbenzoyl chloride (3.92 g) and benzyl alcohol (2.16 g) were refluxed in benzene for 4 hours and then left at room temperature for 48 hours. Removal of the solvent gave the title compound. $\tau$ (CDCl$_3$) 7.9 (3H, s), 6.32 (2H, s), 4.69 (2H, s), 2.78 (2H, d, J=8 Hz), 2.70 (5H, m), 1.99 (2H, d, J=8 Hz).

DESCRIPTION 23

1-(4-Carbomethoxyphenyl)propan-2-one oxime 1-(4-Carbomethoxyphenyl)-2-nitroprop-1-ene (31.0 g) in tetrahydrofuran (900 ml) was stirred with aluminium amalgam, made in the usual way from aluminium (13.5 g) and mercuric chloride (6.9 g). The mixture was cooled in ice and stirring was continued until reaction was complete. The slurry was filtered through celite and the filtrate was evaporated to give a cream solid (17.0 g). $\tau$ (CDCl$_3$) 8.27 (3H, s), 6.22 (2H, s), 6.13 (3H, s), 2.63 (2H, d, J=8 Hz), 1.95 (2H, d, J=8 Hz).

DESCRIPTION 24

1-(4-Carbomethoxy-2-methoxyphenyl)propan-2-one oxime

The title compound was prepared in an identical manner to that described in Description 23 using 1-(4-carbomethoxy-2-methoxyphenyl)-2-nitroprop-1-ene. $\tau$ (CDCl$_3$) 8.27 (3H, s), 6.22 (2H, s), 6.11 (3H, s+3H, s), 2.77 (1H, d, J=8 Hz), 2.45 (1H, s), 2.37 (1H, d, J=8 Hz).

DESCRIPTION 25

1-(4-Carbomethoxy-3-methoxyphenyl)propan-2-one oxime

The title compound was prepared in an identical manner to that described in Description 23 using 1-(4-carbomethoxy-3-methoxyphenyl)-2-nitroprop-1-ene. $\tau$ (CDCl$_3$) 8.2 (3H, s), 6.29 (2H, s), 6.17 (3H, s+3H, s), 3.30 (1H, d, J=8 Hz), 3.15 (1H, s), 2.29 (1H, d, J=8 Hz), 2.29–3.5 (1H, broad).

DESCRIPTION 26

1-(4-Carbomethoxy-2-chlorophenyl)propan-2-one oxime

The title compound was prepared in an identical manner to that described in Description 23 using 1-(4-carbomethoxy-2-chlorophenyl)-2-nitroprop-1-ene. $\tau$ (d$_6$DMSO/CDCl$_3$) 8.22 (3H, s), 6.10 (3H, s+2H, s), 1.8–2.8 (3H, m), 0.2–1.2 (1H, broad).

DESCRIPTION 27

1-(4-Carbomethoxyphenyl)-2-nitroprop-1-ene

4-Carbomethoxybenzaldehyde (101.8 g) with n-butylamine (80.7 ml) were heated in refluxing benzene (500 ml) under a Dean and Stark head until the theoretical amount of water had been collected. The benzene was evaporated and the residual oil was taken up in glacial acetic acid (300 ml). Nitroethane (108.5 ml) was added and the mixture was stirred and heated at 95°–105° for 1 hour. The product crystallised on cooling (87.9 g). $\tau$(CDCl$_3$) 7.58 (3H, s), 6.11 (3H, s), 2.55 (2H, d, 8 Hz), 1.94 (2H, d, 8 Hz), 1.97 (1H, s).

DESCRIPTION 28

1-(3-Carbomethoxyphenyl)-2-nitroprop-1-ene

The title compound was prepared in an identical manner to that described in Description 27 using 3-carbomethoxybenzaldehyde. $\tau$(CDCl$_3$) 8.05 (3H, s), 6.08 (3H, s), 2.25–2.5 (2H, m), 1.7–2.0 (3H, s).

DESCRIPTION 29

1-(3-Carbomethoxy-4-hydroxyphenyl)-2-nitroprop-1-ene

The title compound was prepared in an identical manner to that described in Description 27 using 3-carbomethoxy-4-hydroxybenzaldehyde. $\gamma$(d$_6$DMSO) 7.59 (3H, s), 6.08 (3H, s), 2.94 (1H, d, J=8 Hz), 2.29 (1H, dd, J=8 Hz, J=2 Hz), 2.09 (1H, d, J=2 Hz), 2.0 (1H, s), 0.8 (1H, broad).

DESCRIPTION 30

1-(4-Carbomethoxy-3-hydroxyphenyl)-2-nitroprop-1-ene

The title compound was prepared in an identical manner to that described in Description 27 using 4-carbomethoxy-3-hydroxybenzaldehyde. $\tau$(CDCl$_3$) 7.59 (3H, s), 6.02 (3H, s), 3.07 (1H, d, J=9 Hz), 3.00 (1H, s), 2.1 (1H, d, J=9 Hz), 2.04 (1H, s), −0.02 (1H, s).

DESCRIPTION 31

1-(4-Carbomethoxy-3-methylphenyl)-2-nitroprop-1-ene

The title compound was prepared in an identical manner to that described in Description 27 using 4-carbomethoxy-3-methylbenzaldehyde. $\tau$(CDCl$_3$) 7.6 (8H, s), 7.46 (3H, s), 6.16 (3H, s), 2.5 (1H, d, J=8 Hz), 2.46 (1H, s), 2.08 (1H, d, J=8 Hz), 1.94 (1H, s).

DESCRIPTION 32

1-(4-Carbomethoxy-2-methoxyphenyl)-2-nitroprop-1-ene

The title compound was prepared in an identical manner to that described in Description 27 using 4-carbomethoxy-2-methoxybenzaldehyde. $\gamma$(CDCl$_3$) 7.66 (3H, s), 6.08 (3H, s), 2.68 (1H, d, J=8 Hz), 2.38 (1H, s), 2.29 (1H, d, J=8 Hz), 1.8 (1H, s).

DESCRIPTION 33

1-(4-Carbomethoxy-3-methoxyphenyl)-2-nitroprop-1-ene

The title compound was prepared in an identical manner to that described in Description 27 using 4-carbomethoxy-3-methoxybenzaldehyde. $\tau$(CDCl$_3$) 7.59 (3H, s), 6.2 (3H, s), 6.14 (3H, s) 2.77 (1H, d, J=8 Hz), 2.68 (1H, s), 2.24 (1H, d, J=8 Hz), 1.9 (1H, s).

DESCRIPTION 34

1-(4-Carboethoxyphenyl)-2-nitroprop-1-ene

The title compound was prepared in an identical manner to that described in Description 27 using 4-carboethoxybenzaldehyde. $\tau$(d$_6$DMSO) 8.68 (3H, t, J=7 Hz), 7.62 (3H, s), 5.64 (2H, q, J=7 Hz), 2.3 (2H, d, J=9 Hz), 1.94 (2H, d, J=Hz), 1.86 (1H, s).

DESCRIPTION 35

1-(4-Carbomethoxyphenyl)-2-nitrobut-1-ene

The title compound was prepared in an identical manner to that described in Description 27 using 4-carbomethoxybenzaldehyde and 1-nitropropane. $\tau(d_6DMSO)$ 8.8 (3H, t, J=7 Hz), 8.08 (3H, s), 7.19 (2H, q, J=7 Hz), 6.12 (3H, s), 2.38 (2H, d, J=8 Hz), 1.97 (2H, d, J=8 Hz), 1.97 (1H, s).

DESCRIPTION 36

1-(4-Carboxyphenyl)-2-nitrobut-1-ene

The title compound was prepared in an identical manner to that described in Description 27 using 4-carboxybenzaldehyde and two equivalents of n-butylamine. $\tau(d_6DMSO)$ 7.61 (3H, s), 2.42 (2H, d, J=8 Hz), 2.02 (2H, d, J=8 Hz), 1.95 (1H, s).

DESCRIPTION 37

1-(4-Carbomethoxy-2-fluorophenyl)-2-nitroprop-1-ene

The title compound was prepared in an identical manner to that described in Description 27 using 4-carbomethoxy-2-fluorobenzaldehyde. $\tau(CDCl_3)$ 7.61 (3H, s), 6.02 (3H, s), 2.48 (1H, dd, J=8 Hz, J=8 Hz), 1.95-2.2 (2H, m), 1.85 (1H, s).

DESCRIPTION 38

1-(4-Carbomethoxy-2-chlorophenyl)-2-nitroprop-1-ene

The title compound, mp 74°-77°, was prepared in an identical manner to that described in Description 27 using 4-carbomethoxy-2-chlorobenzaldehyde. $\tau(CDCl_3)$ 7.65 (3H, s), 6.05 (3H, s), 1.6-2.7 (4H, m).

DESCRIPTION 39

4-Carbomethoxy-3-methoxybenzaldehyde

2-Nitropropane (1.0 g) was added to sodium methoxide (from 0.24 g sodium) in methanol (30 ml) and the solution refluxed for ½ hour. 4-Carbomethoxy-3-methoxybenzyl bromide (2.67 g) in methanol was added and the solution refluxed for 1 hour. The methanol was evaporated, the residue partitioned between 2N sodium hydroxide and chloroform. The chloroform layer was shaken with further sodium hydroxide until no more yellow colour was extracted, dried and evaporated to yield the title compound (1.66 g). $\tau(CDCl_3)$ 6.1 (3H, s), 6.05 (3H, s), 2.4-2.6 (2H, m), 2.07 (1H, d, J=8 Hz), −0.05 (1H, s).

DESCRIPTION 40

4-Carbomethoxy-2-methoxybenzaldehyde

The title compound was prepared in an identical manner to that described in Description 39 using 4-carbomethoxy-2-methoxybenzyl bromide. $\tau(CDCl_3)$ 6.1 (3H, s), 6.04 (3H, s), 2.0-2.5 (3H, m), −0.55 (1H, s).

DESCRIPTION 41

4-Carbomethoxy-2-methylbenzaldehyde

The title compound was prepared in an identical manner to that described in Description 39 using 4-carbomethoxy-3-methylbenzyl bromide. $\tau(CDCl_3)$ 7.31 (3H, s), 6.04 (3H, s), 2.15 (1H, d, J=8 Hz), 2.15 (1H, s), 1.89 (1H d, J=8 Hz), −0.09 (1H, s).

DESCRIPTION 42

4-Carbomethoxy-2-fluorobenzaldehyde

The title compound was prepared in an identical manner to that of F Irreverre et al, *J Biol Chem*, 1961, 236, 1093 using methyl-2-fluoro-4-methylbenzoate. $\tau(CDCl_3)$ 6.1 (3H, s), 2.0-2.45 (3H, m), −0.45 (1H, s).

DESCRIPTION 43

4-Carbomethoxy-2-chlorobenzaldehyde

The title compound was prepared in an identical manner to that of Description 39 using 4-carbomethoxy-2-chlorobenzyl bromide. $\tau(CDCl_3)$ 6.06 (3H, s), 1.80-2.15 (3H, m), −0.50 (1H, s).

DESCRIPTION 44

4-Carbomethoxy-3-methoxybenzyl bromide

N-Bromosuccinimide (45.3 g) was added to methyl 2-methoxy-4-methylbenzoate (45.8 g) in carbon tetrachloride (~1 l) containing a trace of dibenzoyl peroxide. The suspension was heated under reflux until no orange colour persisted, then cooled, filtered and the filtrate evaporated to give the title compound, bp 136°-144°/7 mm. $\tau(CDCl_3)$ 6.17 (3H, s), 6.13 (3H, s), 5.59 (2H, s), 2.9-3.15 (2H, m), 2.3 (1H, d, J=8 Hz).

DESCRIPTION 45

4-Carbomethoxy-2-methoxybenzyl bromide

The title compound was prepared in an identical manner to that described in Description 44 using methyl 3-methoxy-4-methylbenzoate. $\tau(CDCl_3)$ 6.1 (3H, s), 6.06 (3H, s), 5.45 (2H, s), 2.2-2.8 (3H, m).

DESCRIPTION 46

4-Carbomethoxy-3-methylbenzyl bromide

N-Bromosuccinimide (44.9 g) was added to a solution of methyl 2,4-dimethylbenzoate (41.36 g) in carbon tetrachloride containing a trace of dibenzoyl peroxide. The mixture was heated under reflux until no orange colour persisted then cooled, filtered and the filtrate evaporated to leave an oil. This was distilled until ~16 g distillate bp 98°-140°/0.8-5 mm (starting material) had been collected. The residue was then heated at atmospheric pressure until no more methyl bromide was evolved, to give a mixture of the title compound and 4-methylphthalide. Addition of hot petrol and filtration from the phthalide gave after evaporation the title compound. $\tau(CDCl_3)$ 7.48 (3H, s), 6.21 (3H, s), 5.65 (2H, s), 2.6-2.93 (2H, m), 2.18 (1H, d, J=8 Hz).

DESCRIPTION 47

4-Carbomethoxy-α-methylbenzylamine hydrochloride

Methyl 4-acetylbenzoate oxime (10 g) was dissolved in ethanol (150 ml) and chloroform (25 ml) and hydrogenated at 75 psi and 60° for 24 hours using platinum oxide as catalyst. The reaction mixture was filtered, the filtrate evaporated and the residue recrystallised from ethyl acetate-methanol to give the title compound, 3 g (1st crop. $\tau(d_6DMSO)$ 8.45 (3H, d, J=7 Hz), 6.18 (3H, s), 5.54 (1H, q, J=7 Hz), 2.34 (2H, d, J=7 Hz), 2.05 (2H, d, J=7 Hz), 1.18 (3H, s, disappears with $D_2O$).

DESCRIPTION 48

1-(S)-(+)-2-(4-Carbomethoxyphenyl)-1-methylethanamine

The title compound was prepared from 1-(S)-(+)-2-phenyl-1-methylethanamine by the method described by F F Blicke and W M Lilienfield, *J Amer Chem Soc*, 1943, 65, 2377 for the ethyl ester. Recrystallisation of the hydrochloride gave colourless needles mp 210°–212°, $\alpha_D^{20}$ +8.9° (5% CH$_3$OH).

DESCRIPTION 49

1-(R)-(−)-2-(4-Carbomethoxyphenyl)-1-methylethanamine

The title compound, mp 210°–211° (methanol-ethyl acetate) $\alpha_D^{20}$ −8.7° (5% CH$_3$OH), was made by the process of Description 48, replacing the 1-(S)-(+) isomer by the 1-(R)-(−) isomer.

DESCRIPTION 50

2-(4-Carbomethoxyphenyl)-1-methylethanamine 1-(4-Carbomethoxyphenyl)propan-2-one oxime (10.0 g) in absolute alcohol (200 ml) and chloroform (25 ml) was hydrogenated on a Parr hydrogenator at 50 psi and at 50° in the presence of platinum oxide (250 mg) until hydrogen uptake had ceased. The catalyst was removed and the residue was recrystallised as the hydrochloride from methanol/ethyl acetate, mp 206°–210° (8.5 g). γ(d$_6$DMSO) 8.84 (3H, d, 6 Hz), 6.2–7.5 (3H, m), 6.17 (3H, s), 2.59 (2H, d, J=8 Hz), 2.09 (2H, d, J=8 Hz), 1.50 (2H, br).

DESCRIPTION 51

2-(4-Carbomethoxyphenyl)ethanamine

The title compound, mp 225°–228° (methanol) was made as the hydrochloride by the process of Description 48 replacing the 1-(S)-(+)-2-phenyl-1-methylethanamine by 2-phenylethanamine. γ(d$_6$DMSO) 6.65–7.15 (4H, m), 6.17 (3H, s), 2.65 (2H, d, J=8 Hz), 2.13 (2H, d, J=8 Hz), 1.63 (2H, br).

DESCRIPTION 52

2-(4-Carbomethoxyphenyl)-1,1-dimethylethanamine

The title compound, mp 196°–198° (methanol-ethyl acetate) was made as the hydrochloride by the process of description 48, replacing 1-(S)-(+)-2-phenyl-1-methylethanamine by 1,1-dimethyl-2-phenylethanamine. γ(d$_6$DMSO) 8.74 (6H, s), 6.93 (2H, s), 6.15 (3H, s), 2.56 (2H, d, J=8 Hz), 2.05 (2H, d, J=8 Hz), 1.54 (2H, br).

DESCRIPTION 53

N-Benzyl-2-[4-carbomethoxyphenyl]-1-methylethanamine 1-(4-Carbomethyoxyphenyl)propan-2-one (8.2 g) and benzylamine (4.5 g) were heated in refluxing benzene (150 ml) under a Dean and Stark head until complete removal of water. The solvent was replaced with methanol and the mixture was stirred and cooled during portionwise addition of sodium borohydride (5.0 g). The mixture was stirred for 2 hours, evaporated and the residue was partitioned between water and ether. Evaporation of the dried organic extract gave a yellow oil which was converted to the hydrochloride salt, mp 189°–192° (methanol-ethyl acetate). γ(CDCl$_3$) 8.90 (3H, d, J=6 Hz), 6.90–7.50 (4H, m), 6.25 (2H, s), 6.19 (3H, s), 2.50–3.00 (7H, m), 2.15 (2H, d, J=8 Hz).

DESCRIPTION 54

4-Benzyloxy-3-hydroxymethylphenylglyoxal 1-(4-Benzyloxy-3-hydroxymethylphenyl)ethanone (10.4 g) was added portionwise to a stirred solution of selenium dioxide (5.5 g) in water (0.9 ml) and dioxan (100 ml) at 60°. The mixture was stirred under reflux for 4 hours, filtered whilst hot and allowed to cool. The solid was collected and recrystallised from dioxan as a dimer, mp 180°–181° (7.7 g). (d$_6$DMSO) 5.13 (1H, s), 4.94 (1H, s), 4.72 (2H, s), 3.42 (1H, d, J=10 Hz), 3.24 (1H, d, J=10 Hz), 2.72 (1H, m), 2.54 (5H, m), 2.04 (1H, m), 1.46 (1H, m).

DESCRIPTION 55

4-Benzyloxy-3-methanesulphonamidophenyl glyoxal

The compound was obtained as an ethanol hemiacetal, mp 125°–128° (ethanol-water) by the process of Description 54 replacing 1-(4-benzyloxy-3-hydroxymethylphenyl)ethanone by 1-(4-benzyloxy-3-methanesulphonamidophenyl)ethanone. (CDCl$_3$) 8.75 (3H, t, J=6 Hz), 7.05 (3H, s), 5.90–6.40 (2H, m), 4.90 (1H, b), 4.80 (2H, s), 4.46 (1H, s), 2.90 (1H, d, J=8 Hz), 2.60 (5H, s), 2.20 (1H, s), 2.09 (1H, dd, J=8 Hz, 2 Hz), 1.80 (1H, d, J=2 Hz).

DESCRIPTION 56

3-Acetamido-4-benzyloxyphenyl glyoxal

The title compound was obtained as a hydrate, mp 123°–128° (dioxan-ether) by the process of Description 54. replacing 1-(4-benzyloxy-3-hydroxymethylphenyl)ethanone by 1-(3-acetamido-4-benzyloxyphenyl)ethanone. τ(d$_6$DMSO) 7.74 (3H, s), 6.66 (2H, s), 7.88 (2H, s), 1.80–3.10 (7H, m), 1.45 (1H, m), 1.05 (1H, d, J=2 Hz).

DESCRIPTION 57

4-Benzyloxy-3-nitrophenyl glyoxal 1-(4-Benzyloxy-3-nitrophenyl)-2-bromoethanone (12.6 g) was dissolved in dimethyl sulphoxide (40 ml) and the solution was allowed to stand at room temperature for 3 days. The solution was poured onto ice and the product was collected as the hydrate (8.7 g). τ(d$_6$DMSO) 4.58 (2H, s), 4.33 (1H, s), 2.25–2.65 (6H, m), 2.07 (2H, br), 1.30–1.87 (2H, m).

DESCRIPTION 58

4-Amino-3,5-dichlorophenyl glyoxal

The title compound was obtained as the ethanol hemiacetal, mp 51°–54° (ethanol-water) by the process of Description 57 replacing 1-(4-benzyloxy-3-nitrophenyl)-2-bromoethanone by 1-(4-amino-3,5-dichlorophenyl)-2-bromoethanone. τ(d$_6$DMSO) 8.85 (3H, t, J=6 Hz), 6.00–6.50 (2H, m), 4.62 (1H, d, J=8 Hz), 3.56 (2H, b), 3.05 (1H, d, J=8 Hz), 2.12 (2H, s).

DESCRIPTION 59

3,5-Dibenzyloxyphenyl glyoxal

The title compound was prepared as a hydrate by the process of Description 54, replacing 1-(4-benzyloxy-3-hydroxymethylphenyl)ethanone. by 1-(3,5-dibenzyloxyphenyl)ethanone. γ(CDCl$_3$) 6.40 (2H, s) 5.00 (4H, s), 2.40–3.50 (14H, m).

DESCRIPTION 60

1-(3,4-Dicarbomethoxyphenyl)propan-2-one

The title compound was prepared in an identical manner to that described in Description 1, using 1-(3,4-dicarbomethoxyphenyl)propan-2-one oxime. $\tau(CDCl_3)$ 7.84 (3H, s) 6.24 (2H, s), 6.14 (6H, s), 2.2–2.8 (3H, m).

DESCRIPTION 61

1-(3,4-Dicarbomethoxyphenyl)propan-2-one oxime

The title compound was prepared in an identical manner to that described in Description 23, using 1-(3,4-dicarbomethoxyphenyl)-2-nitroprop-1-ene. $\tau(CDCl_3)$ 8.22 (3H, s), 6.23 (2H, s), 6.12 (6H, s), 2.1–2.9 (3H, m), 0.5–1.5 (1H, broad).

DESCRIPTION 62

1-(3,4-Dicarbomethoxyphenyl)-2-nitroprop-1-ene

The title compound was prepared in an identical manner to that described in Description 27, using 3,4-dicarbomethoxybenzaldehyde. $\tau(CDCl_3)$ 7.6 (3H, s), 4.1 (6H, s), 1.5–2.8 (4H, m).

DESCRIPTION 63

3,4-Dicarbomethoxybenzaldehyde

The title compound was prepared in an identical manner to that described in Description 39, using 3,4-dicarbomethoxybenzylbromide. $\tau(CDCl_3)$ 6.10 (6H, s), 1.7–2.5 (3H, m) −1.1 (1H, s).

DESCRIPTION 64

3,4-Dicarbomethoxybenzyl bromide

The title compound was prepared in an identical manner to that described in Description 44, using dimethyl-4-methylphthalate. $\tau(CDCl_3)$ 6.12 (6H, s) 5.53 (2H, s). 2.1–2.8 (3H, m).

DEMONSTRATION 1

(a) Demonstration of Effectiveness of Compounds (i) The compounds and a comparison compound (salbutamol) were dosed daily in water or carboxymethylcellulose suspension to genetically obese mice by oral gavage for 28 days. At the end of that time the carcass composition was determined. The results obtained were as follows:

| Compound of Example | Dose mg/kg po | g - lipid per mouse Treated | g - lipid per mouse Control |
|---|---|---|---|
| 1 | 8 | 20.8 ± 0.7 | 23.3 ± 0.7 |
| 7 | 10 | 14.3 ± 0.4 | 18.3 ± 0.6 |
| 8 | 21 | 19.6 ± 0.4 | 21.9 ± 0.5 |
| 12 | 11 | 16.2 ± 0.42 | 18.9 ± 0.66 |
| 14 | 10.5 | 14.3 ± 0.61 | 17.0 ± 0.67 |
| 16 | 10 | 12.9 ± 0.8 | 16.5 ± 0.7 |
| 17 | 11 | 14.0 ± 0.97 | 17.0 ± 0.67 |
| 21 (mp 140.5-143.5°) | 10 | 12.7 ± 0.8 | 16.5 ± 0.7 |
| 22 | 9 | 13.9 ± 0.65 | 18.9 ± 0.66 |
| 26 | 9 | 16.4 ± 1.2 | 18.9 ± 0.66 |
| 28 | 19 | 14.9 ± 0.37 | 17.0 ± 0.67 |
| 30 | 22 | 14.0 ± 0.57 | 19.1 ± 0.47 |
| Salbutamol | 25 | 23.1 ± 0.6 | 23.0 ± 0.3 |

(ii) Hypoglycaemic activity

Female CFLP mice, weighing approximately 25 g, were fasted for 24 hours prior to the study. The compounds under study were dosed orally (20 mg and 5 mg/kg) to to each of 8 mice. 30 minutes later a blood sample (20 ml) was obtained from the tail for the analysis of blood glucose. Immediately after taking this blood sample, each mouse was given a glucose load (1 g/kg body weight sub-cutaneously). Blood samples were then obtained from each mouse at 30 minute intervals for 120 minutes.

Compounds that produced a significant (P<0.05) reduction of blood glucose, compared with control mice given water, at any time interval were considered active. The area under the blood glucose curve over the 2 hour period after giving the glucose load was calculated for each compound and compared with the value for control animals. Thus a compound would give a 100% reduction in the area under the blood glucose curve if the blood glucose was maintained at the same level as in untreated fasted animals. Reduction in the glucose curve of more than 100% indicate that a compound, in spite of being given a glucose load, maintained blood glucose levels below that found in control fasted mice.

| Compound of Example | Dose mg/kg po | Reduction in area under blood glucose curve (%) |
|---|---|---|
| 1 | 5 | 157 |
| 7 | 5 | 110 |
| 9 | 5 | 47 |
| 12 | 5 | 168 |
| 17 | 5 | 84 |
| 18 | 20 | 25 |
| 21 (mp 140.5–143.5°) | 5 | 153 |
| 22 | 5 | 172 |
| 25 | 5 | 179 |
| 27 | 5 | 38 |
| 28 | 5 | 37 |
| 30 | 5 | 141 |
| 31 | 5 | 139 |
| 33 | 5 | 88 |
| 34 | 20 | 61 |
| 36 | 5 | 79 |
| 38 | 5 | 59 |
| 39 | 5 | 83 |

(b) Acute Toxicity

The single lethal dose of the compound of Example 1 in CFLP mice was found to be >900 mg/kg po. Other compounds of the invention have similar low toxicities.

(c) Bronchodilator Activity

Comparison in vivo of the bronchodilator potency of the compound of Example 1 and salbutamol in the anaesthetised artificially respired guinea pig (Konzett-Rossler preparation) showed that the compound of Example 1 was only one twelfth as potent as salbutamol in inibiting 5-hydroxytryptamine-induced bronchoconstriction.

We claim:

1. A pharmaceutical composition useful for the treatment of obesity or hyperglycaemia in humans and animals which comprises an anti-obesity effective amount or an anti-hyperglycaemically effective amount of a compound of the formula (II):

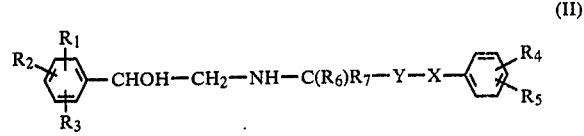

(II)

or a pharmaceutically acceptable salt thereof, wherein $R_1$ is hydrogen, fluorine, chlorine, hydroxy, hydroxymethyl, methyl, methoxyl, amino, formamido, acetamido, methylsulphonylamido, nitro, benzyloxy, methylsulphonylmethyl, ureido, trifluoromethyl or p-methoxybenzylamino; $R_2$ is hydrogen, fluorine, chlorine or hydroxyl; $R_3$ is hydrogen, chlorine or methoxyl; $R_4$ is carboxylic acid or a salt, ester or amide thereof; $R_5$ is hydrogen, chlorine, fluorine, methyl, ethyl, methoxyl or hydroxyl or carboxylic acid or a salt, ester or amide thereof; $R_6$ is hydrogen, methyl, or propyl; X is oxygen or a bond; $R_7$ is hydrogen, methyl, ethyl or propyl and Y is alkylene of up to 6 carbon atoms or a bond, in combination with a pharmaceutically acceptable carrier.

2. A composition according to claim 1 wherein $C(R_6)R_7$ is $CH(CH_3)$.

3. A composition according to claim 1 wherein n is alkylene having 1 to 3 carbon atoms.

4. A composition according to claim 1 wherein $R_4$ is a group of the sub-formula (a), (b) or (c):

—$CO_2H$ (a)

—$CO_2{}^1/_qA^{q+}$ (b)

—$CO_2R_8$ (c)

where $A^{q+}$ is an ion wherein q is 1 or 2; and $R^8$ is a group such that $CO_2R^8$ is an ester group.

5. A composition according to claim 1 wherein the compound is in the form of a single stereoisomer.

6. A composition according to claim 1 wherein the compound is in the form of a mixture of stereoisomers.

7. A composition according to claim 1 wherein the compound contains two centres of asymmetry and is used as a diasterioisomer free of the other diastereoisomer.

8. A composition according to claim 1 wherein $R_6$ is hydrogen.

9. A composition according to claim 1 wherein $R_6$ is methyl.

10. A composition according to claim 1 wherein $R_7$ is hydrogen.

11. A composition according to claim 1 wherein $R_7$ is methyl.

12. A composition according to claim 1 wherein $R_5$ is hydrogen.

13. A composition according to claim 1 wherein $R_5$ is a lower alkyl ester group.

14. A composition according to claim 1 wherein $R_5$ is methyl, ethyl, or n-propyl.

15. A composition according to claim 1 wherein $R_5$ is alkyl of 1 to 4 carbon atoms.

16. A composition according to claim 1 in oral administration form.

17. A composition according to claim 1 in a form suitable for administration by injection.

18. A composition according to claim 1 in unit dosage form, wherein each dosage unit contains from 0.01 to 100 milligrams of said compound.

19. A method of treating obesity in humans and animals and treating hyperglycaemia in humans and animals, which comprises administering to a human or animal in need thereof, an anti-obesity effective amount or an anti-hyperglycaemically effective amount of a composition of claim 1.

20. A method according to claim 19 wherein $R_1R_2R_3$ are each hydrogen.

21. A method according to claim 19 wherein $C(R_6)R_7$ is $CH(CH_3)$.

22. A method according to claim 19 wherein n is alkylene of 1 to 3 carbon atoms.

23. A method according to claim 19 wherein $R_4$ is a group of the sub-formula (a), (b) or (c):

—$CO_2H$ (a)

—$CO_2{}^1/_qA^{q+}$ (b)

—$CO_2R_8$ (c)

where $A^{q+}$ is an ion wherein q is 1 or 2; and $R^8$ is a group such that $CO_2R^8$ is an ester group.

24. A method according to claim 23 wherein $R_8$ is lower alkyl, lower alkyl substituted by hydroxyl not on the α-carbon atom or a group of the sub-formulae (q) or (r):

—$CHR_{10}$—O—CO—$R_{11}$ (q)

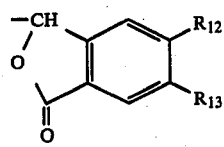 (r)

wherein $R_{10}$ is hydrogen or methyl, $R_{11}$ is lower alkyl or phenyl; $R_{12}$ is hydrogen, methyl or methoxyl; and $R_{13}$ is hydrogen, methyl or methoxyl.

25. A method according to claim 23 wherein $R_8$ is methyl, ethyl, propyl, butyl, pentyl or hexyl.

26. A method according to claim 19 wherein $R_4$ is in the para-position.

27. A method of treating obesity and hyperglycaemia in humans and animals, which comprises administering to a human or animal in need thereof, an anti-obesity effective amount or an anti-hyperglycaemically effective amount of a compound of the formula (III):

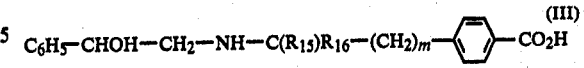 (III)

$C_6H_5$—CHOH—$CH_2$—NH—$C(R_{15})R_{16}$—$(CH_2)_m$—⟨⟩—$CO_2H$ or a pharmaceutically acceptable salt or ester thereof wherein $R_{15}$ is hydrogen or methyl; $R_{16}$ is hydrogen or methyl; and m is 1, 2 or 3.

28. A method according to claim 19 wherein $R_6$ is methyl.

29. A method according to claim 19 wherein the compound is in the form of a single stereoisomer.

30. A method according to claim 19 wherein the compound is in the form of a mixture of stereoisomers.

31. A method according to claim 19 wherein the compound contains two centres of asymmetry and is used as a diastereoisomer free of the other diastereoisomer.

32. A method according to claim 19 wherein $R_6$ is hydrogen.

33. A method according to claim 19 wherein $R_7$ is hydrogen.

34. A method according to claim 19 wherein $R_7$ is methyl.

35. A method according to claim 19 wherein $R_5$ is hydrogen.

36. A method according to claim 23 wherein $R_8$ is methyl, ethyl, n-propyl, isopropyl, n-butyl, iso-butyl, sec-butyl, t-butyl, pentyl, hexyl, benzyl, phenyl, acetoxymethyl, pivaloyloxymethyl, α-ethoxycarbonyloxyethyl or phthalidyl.

37. A method according to claim 23 wherein $R_8$ is methyl, ethyl, n-propyl, acetoxymethyl, pivaloyloxymethyl, α-ethoxycarbonyloxethyl or phthalidyl.

38. A method according to claim 23 wherein $R_8$ is alkyl of 1 to 4 carbon atoms.

39. A method according to claim 19 wherein the administration is oral.

40. A method according to claim 19 wherein the administration is by injection.

* * * * *